US006576428B1

(12) United States Patent
Assenmacher et al.

(10) Patent No.: US 6,576,428 B1
(45) Date of Patent: Jun. 10, 2003

(54) DIRECT SELECTION OF ANTIGEN-SPECIFIC T CELLS, COMPOSITIONS OBTAINED THEREBY AND METHODS OF USE THEREOF

(75) Inventors: Mario Assenmacher, Bergisch Gladbach (DE); Stefan Miltenyi, Bergisch Gladbach (DE); Jurgen Schmitz, Bergisch Gladbach (DE)

(73) Assignee: Miltenyi Biotech GmbH (DE)

( * ) Notice: Subject to any disclaimer, the term of this patent is extended or adjusted under 35 U.S.C. 154(b) by 0 days.

(21) Appl. No.: 09/309,199

(22) Filed: May 10, 1999

Related U.S. Application Data

(60) Provisional application No. 60/085,136, filed on May 11, 1998.

(51) Int. Cl.[7] ............................. G01N 33/53; C12N 5/00

(52) U.S. Cl. ...................... 435/7.1; 435/7.24; 435/373; 435/383

(58) Field of Search ................................ 435/7.1, 7.24, 435/373, 383

(56) References Cited

U.S. PATENT DOCUMENTS

| | | | |
|---|---|---|---|
| 4,230,685 A | 10/1980 | Senyei et al. |
| 4,452,773 A | 6/1984 | Molday |
| 4,770,183 A | 9/1988 | Groman et al. |
| 5,385,707 A | 1/1995 | Miltenyi et al. |
| 5,411,863 A | 5/1995 | Miltenyi |
| 5,543,289 A | 8/1996 | Miltenyi |
| 5,635,363 A | 6/1997 | Altman et al. |
| 5,693,539 A | 12/1997 | Miltenyi et al. |
| 5,750,356 A | 5/1998 | Spack et al. |

FOREIGN PATENT DOCUMENTS

| | | |
|---|---|---|
| WO | WO 85/04330 | 10/1985 |
| WO | WO 90/02334 | 3/1990 |
| WO | PCT/EP89/01602 | 7/1990 |
| WO | PCT/US93/10126 | 4/1994 |
| WO | WO 94/09117 * | 4/1994 |
| WO | WO 96/37208 | 11/1996 |
| WO | WO 97/05239 | 2/1997 |
| WO | WO 97/35035 | 9/1997 |
| WO | WO 97/46256 | 12/1997 |

OTHER PUBLICATIONS

Manz et al. (Proc.Natl.Acad.Sci., 1995, 92, 1921–1925.).*
Assenmacher et al. (Eur.J. Immunol.1998, 28, 1534–1543).*
Peyret, C. et al. (1991). "Adoptive Immunotherapy and Metastasized Cancer of Kidney: Regulating Effects of Interleukin–4 on Tumor–Infiltrating Lymphocytes (TIL)," *Chirurgie* 117:700–709. (Full translation provided).
U.S. patent application Ser. No. 08/416,920, Miltenyi et al. filed Apr. 21, 1995.
U.S. patent application Ser. No. 08/441,279, a Continuation Application of 07/965,934 filed Oct. 21, 1992, Miltenyi et al. May 15, 1995.
Assenmacher, M. et al. (1998). "Sequential Production of IL–2, IFN–γ, and IL–10 by Individual Staphylococcal Enterotoxin B–Activated T Helper Lymphocytes," *Eur. J. Immunol.* 28:1534–1543.
Brosterhus, H. et al. (1999). "Enrichment and Detection of Live Antigen–Specific CD4+ and CD8+ T Cells Based on Cytokine Secretion," *Eur. J. Immunol.* 29:4053–4059.
Assenmacher et al. (1995) "Fluorescence–activated cytometry cell sorting based on immunological recognition" *Clin. Biochem.* 28:39–40.
Manz et al. (1995) "Analysis and sorting of live cells according to secreted molecules located to a celll surface affinity matrix" *Proc. Natl. Acad. Sci. USA* 92:1921–1925.
International Search Report on International Application No. PCT/US99/10200.
Alkan et al. (1994) "Chemiluminescent and enzyme–linked immuno assays for sensitive detection of human IFN–γ" *J. Immunoassay* 15:217–238.
Altman et al. (1996) "Phenotypic analysis of Antigen–specific T lymphocytes" *Science* 274:94–96.
Bird et al. (1991) "Development of immunoassays for human interleukin 3 and interleukin 4, some of which discriminate between different recombinant DNA–derived molecules" *Cytokine* 3:562–567.
Brosterhus et al. (1998) 10th International Congress In Immunology 1479–1473.
Dunbar et al. 91998) "Direct isolation, phenotyping and cloning of low–frequency antigen–specific cytotoxic T lymphocytes from peripheral blood" *Current Biology* 8:413–416.
Ebers (1994) "Treatment of multiple sclerosis" *Lancet* 343:275–279.
El Ghazali et al. (1993) "Number of interleukin–4 and interferon–γ–secreting human T cells reactive with tetanus toxoid and the mycobacterial antigen PPD or phytohemagglutinin: distinct response profiles depending on the type of antigen used for activation" *Curr Opin Immunol* 23:2740–2745.

(List continued on next page.)

Primary Examiner—Christina Chan
Assistant Examiner—Michail Belyavskyi
(74) Attorney, Agent, or Firm—Morrison & Foerster LLP

(57) ABSTRACT

The invention provides a method for convenient analysis and cell separation of antigen-specific T cells based on one or more products secreted by these cells in response to antigen stimulation. The T cells are provided with a capture moiety for the product, which can then be used directly as a label in some instances, or the bound product can be further labeled via label moieties that bind specifically to the product and that are labeled with traditional labeling materials such as fluorophores, radioactive isotopes, chromophores or magnetic particles. The labeled cells are then separated using standard cell sorting techniques based on these labels. Such techniques include flow cytometry, magnetic gradient separation, centrifugation, and the like.

19 Claims, 15 Drawing Sheets

OTHER PUBLICATIONS

Flynn et al. (1988) "Virus Specific CD8+ T Cells in Primary and Secondary Influenza Pneumonia" *Immunity* 8:663–691.

Gallimore et al. (1998) "Introduction and Exhaustion of Lymphocytic Choriomeningitis Virus–specific Cytotocix T Lymphocytes Visualized Using Soluble Tetrameric Major Histocompatibility Complex Class I–Peptide Complexes" *J. Exp. Med.* 18:1383–1393.

Hafler et al. (1992) "T Cell vaccination in multiple sclerosis: a preliminary report" *Clinical Immunol. Immunopath.* 62:307–313.

Hamann et al. (1997) "Phenotypic and Functional separation of memory and effector human CD8+ T cells" *J. Exp Med* 186:1407–1418.

Heslop et al. (1996) "Long–term restoration of immunity against Epstein–Barr virus infection by adoptive transfer of gene–modified virus–specific T lymphocytes" *Nature Medicine* 2:551–555.

Hohlfeld (1997) "Biotechnological agents for the immunotherapy of multiple sclerosis, principles, problems and perspectives" *Brain* 120:865–916.

Huang et al. (1994) "Protein Transfer of Performed MHC–Peptide Complexes Sensitizes Target Cells to T cell Cytolysis" *Immunity* 1:607–613.

Kern et al. (1998) "T–Cell epitope mapping by flow cytometry" *Nature Medicine* 4:975–978.

Köhler et al. (1980) "Immunoglobulin M mutants" *J. Immunol* 1:467–476.

Lalvani et al. (1997) "Rapid Effector Function in CD8+ Memory T Cells" *J. Exp. Med.* 186:859–865.

Lehner et al. (1995) "Human HLA–A0201–restricted cytotoxic T lymphocyte recognition of influenza A is dominated by T cells bearing the Vβ17 gene segment" *J Exp Med* 181:79–91.

Luxembourg et al. (1998) "Biomagnetic isolation of antigen–specific CD8$^{+cells}$ useable in immunotherapy" *Nature Biotech* 16:281–285.

Mattis et al. (1997) "Analyzing cytotoxic T Lymphocyte activity: a simpler and reliable flow cytometry–based assay" *J. Immunological Methods* 204:135–142.

Meager et al. (1984) "Detection of Hybridomas Secreting Monoclonal Antibodies to Human Gamma Interferon Using a Rapid Screening Technique and Specificity of Certain Monoclonal Antibodies to Gamma Interferon" *J. Interferon Research* 4:619–625.

Medof et al. (1984) "Inhibition of complement activation of cells after incorporation of decay–accelerating factor (DAF) into their membranes" *J. Exp. Med* 160:1558–1578.

Miyahira et al. (1995) "Quantification of antigen specific CD8+ T cells using an ELISPOT assay" *J. Immunol Met* 181:45–54.

Murali–Krishna et al. (1998) "Counting Antigen–Specific CD8 T Cells: A Reevaluation of ByStander Activation during Viral Infection" *Immunity* 8:177–187.

Nir et al. (1990) "Single–Cell Entrapment and Microcolony Development within Uniform Microspheres Amenable to Flow Cytometry" *Appl Env Microbiol* 2870–2875.

Nir et al. (1990) "Flow Cytometry Sorting of Viable Bacteria and Yeasts According to β–Galactosidase Activity" *App Env Microbiol* 3861–3866.

Ogg et al. (1998) "Quantification of HIV–1–specific cytotoxic T lymphocytes and plasma load of viral RNA" *Science* 279:2103–2106.

Peyret et al. (1991) "Immunothérapie adoptive et cancer du rein métastasé" *Chirurgie* 117:700–709, Abstract Only.

Salmon et al. (1989) "Production of Lymphokine mRNA by CD45R+ and CD45R$^{31}$ Helper T Cells from Human Peripheral Blood and by Human CD4+ T Cell Clones" *J. Immunology* 143:907–912.

Sporn et al. (1993) "Adoptive immunotherapy with peripheral blood lymphocytes cocultured in vitro with autologous tumor cells and interleukin–2" *Cancer Immunol Immunother* 37:175–180.

Triozzi (1993) "Identification and Activation of Tumor–Reactive Cells for Adoptive Immunotherapy" *Stem Cells* 11:204–211.

Sussman et al. (1994) "Activation of T Lymphocytes for the Adoptive Immunotherapy of Cancer" *Ann. Surgical Oncology* 1:296–306.

Waldrop et al. (1997) "Determination of Antigen–specific Memory/Effector CD4+ T Cell Frequencies by Flow Cytometry" *J. Clin. Invest* 99:1739–1750.

Weidmann et al. (1994) "Relevance of the T cell receptor for immunotherapy of cancer" *Cancer Immunol Immunother* 39:1–14.

Yee et al. (1997) "Prospects for adoptive T cell therapy" *Curr Opinion Immunol* 9:702–708.

Zweerink et al. (1993) "Presentation of Endogenous Peptides to MHC Class I–Restricted Cytotoxic T Lymphocytes in Transport Deletion Mutant T2 Cells" *J. Immunol.* 150:1763–1771.

* cited by examiner

CD57

V$_\beta$17

CD57

V$_\beta$17

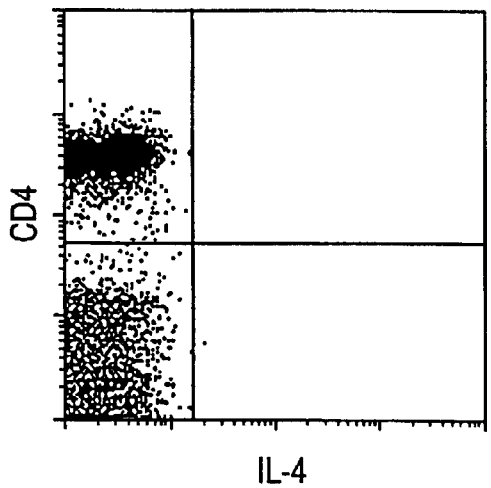
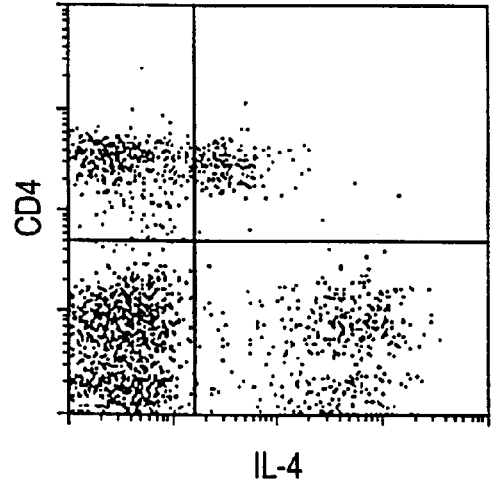
FIG. 6A
FIG. 6B
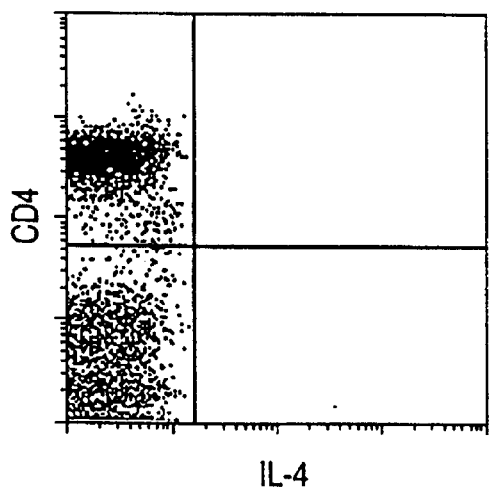
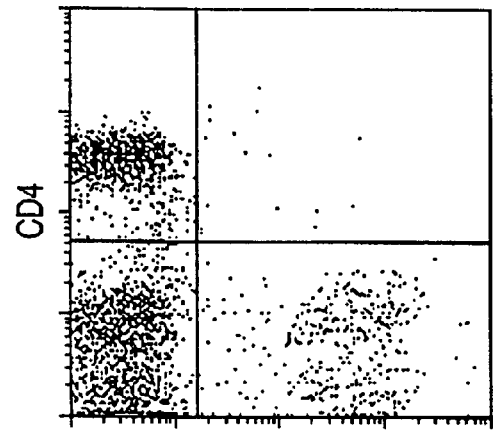
FIG. 6C
FIG. 6D

DIRECT SELECTION OF ANTIGEN-SPECIFIC T CELLS, COMPOSITIONS OBTAINED THEREBY AND METHODS OF USE THEREOF

CROSS-REFERENCE TO RELATED APPLICATIONS

This is a continuation in part of U.S. Serial No. 60/085,136 filed May 11, 1998.

STATEMENT OF RIGHTS TO INVENTIONS MADE UNDER FEDERALLY SPONSORED RESEARCH

Not Applicable

1. Technical Field

The invention is in the field of analysis of cell populations and cell separation and the compositions obtained thereby. More particularly, the invention concerns analysis and separation of antigen-specific T cells based on primary labeling of cells with their secreted products through capture of these products by a specific binding partner for the product anchored or bound to the cell surface.

2. Background Art

Numerous attempts have been made to analyze populations of cells and to separate cells based on the products which they produce. Such approaches to cell analysis and separation are especially useful in assessing those cells which are capable of secreting a desired product (the "product"), or which are relatively high secretors of the product. These methods include cloning in microtiter plates and analysis of the culture supernatant for product, cloning in agar and analysis by methods for identification of the product of the localized cells; the identification methods include, for example, plaque assays and western blotting. Most methods for analysis and selection of cells based upon product secretion involve physically isolating the cell, followed by incubation under conditions that allow product secretion, and screening of the cell locations to detect the cell or cell clones that produce the product. When cells are in suspension, after the cells have secreted the product, the product diffuses from the cell without leaving a marker to allow identification of the cell from which it was secreted. Thus, secretor cells cannot be separated from non-secretor cells with these types of systems.

In other cases, both secretor and non-secretor cells can associate the product with the cell membrane. An example of this type of system are B cell derived cell lines producing monoclonal antibodies. It has been reported that these types of cell lines were separated by fluorescence activated cell sorting (FACS) and other methods reliant upon the presence of antibody cell surface markers. However, procedures that analyze and separate cells by markers that are naturally associated with the cell surface can not accurately identify and/or be used in the separation of secretor cells from non-secretor cells. In addition, systems such as these are not useful in identifying quantitative differences in secretor cells (i.e., low level secretors from high level secretors).

A method that has been used to overcome the problems associated with product diffusion from the cells has been to place the cell in a medium that inhibits the rate of diffusion from the cell. A typical method has been to immobilize the cell in a gel-like medium (agar), and then to screen the agar plates for product production using a system reliant upon blotting, for example Western blots. These systems are cumbersome and expensive if large numbers of cells are to be analyzed for properties of secretion, non-secretion, or amount of secretion.

Köhler et al. have described a negative-selection system in which mutants of a hybridoma line secreting IgM with anti-trinitrophenyl (anti-TNP) specificity were enriched by coupling the hapten (i.e., TNP) to the cell surface and incubating the cells in the presence of complement. In this way, cells secreting wild-type Ig were lysed, whereas cells secreting IgM with reduced lytic activity or not binding to TNP preferentially survived. Köhler and Schulman (1980) *Eur. J. Immunol.* 10:467–476.

More recently, a system has been described for labeling and separating cells based on secreted product. PCT/US93/10126. In this system, a specific binding partner for a secreted product is coupled to the surface of cells. The product is secreted, released, and bound to the cell by the specific binding partner. Cells are then separated based on the degree to which they are labeled with the bound product.

Other systems allow the cells to secrete their products in the context of microdroplets of agarose gel which contain reagents that bind the secretion products, and encapsulation of the cells. Such methods have been disclosed in publications by Nir et al. (1990) *Applied and Environ. Microbiol.* 56:2870–2875; and Nir et al. (1991) *Applied and Environ. Microbiol.* 56:3861–3866. These methods are unsatisfactory for a variety of reasons. In the process of microencapsulation, statistical trapping of numbers of cells in the capsules occurs, resulting in either a high number of empty capsules when encapsulation occurs at low cell concentrations, or multiple cells per capsule when encapsulation occurs at high cell concentrations. Secreted product is trapped in the agarose drop by the capture antibody and detected by a second fluorochromated antibody. This process, while allowing for the detection and isolation of cells based on secreted product, is complicated, requires special equipment, and is not suited to all types of sorting methods. In order to analyze and separate single cells or single cell clusters by this technique, large volumes must be handled to work with relatively small numbers of cells because of the numbers of empty capsules and because of the size of the microcapsules (50–100 μm). The large volume of droplets results in background problems using flow cytometry analysis and separation. In addition, the capsules do not allow separation using magnetic beads or panning for cell separation.

Various methods have been used to couple labels to cell surfaces where the label such as a fluorochrome is intended for direct detection. For example, hydrophobic linkers inserted into the cell membrane to couple fluorescent labels to cells have been described in PCT WO 90/02334, published Mar. 8, 1990. Antibodies directed to HLA have also been used to bind labels to cell surfaces. Such binding results in a smaller dimension than the encapsulated droplets described above and such cells can be conveniently used in standard separation procedures including flow cytometry and magnetic separations.

ELISpot assays and methods for intracellular cytokine staining have been used for enumeration and characterization of antigen-specific $CD4^+$ and $CD8^+$ T cells. Lalvani et al. (1997) *J. Exp. Med.* 186:859–865; and Waldrop et al. (1997) *J. Clin Invest.* 99:1739–1750. These methods can be quite useful for T-cell epitope mapping or for monitoring immunogenicity in vaccine trials, but they do not allow isolation of live antigen-specific T cells, e.g., for clinical trials of specific adoptive immunotherapy of cancer or infections. Kern et al. (1998) *Nat. Med.* 4:975–978; E1

Ghazali et al. (1993) *Curr. Opin Immunol.* 23:2740–2745; and Yee et al (1997) *Curr. Opin. Immund.* 9:702–708. Soluble multivalent complexes of peptide-loaded major histocompatibility complex (MHC) molecules have been exploited recently to detect and also isolate antigen-specific T cells. Altman et al. (1996) *Science* 274:94–96; Dunbar et al. (1998) *Curr. Biol.* 8:413–416; Ogg et al. (1998) 279:2103–2106; Luxembourg et al. (1998) *Nat. Biotechnol.* 16:281–285; Murali-Krishna et al. (1998) *Immunity* 8:177–187; Gallimore et al. (1998) *J. Exp. Med.* 187:1383–1393; and Flynn et al. (1998) *Immunity* 8:683–691. These reagents are highly specific but the approach is limited to well defined combinations of antigenic peptides and restricting HLA alleles.

The immune system comprises two types of antigen-specific cells: B cells and T cells. T cells can be characterized phenotypically by the manner in which they recognize antigen, by their cell surface markers, and by their secreted products. Unlike B cells, which recognize soluble antigen, T cells recognize antigen only when the antigen is presented to them in the form of small fragments bound to major histocompatibility complex (MHC) molecules on the surface of another cell. Any cell expressing MHC molecules associated with antigen fragments on its surface can be regarded as an antigen-presenting cell (APC). In most situations, however, more than the mere display of an MHC-bound antigen fragment on a cell surface is required to activate a T lymphocyte. In addition to the signal delivered via the T cell receptor (TCR) engaged by MHC molecule plus antigen, the T cell must also receive co-stimulatory signals from the APC. Typically APCs are dendritic cells, macrophages or activated B lymphocytes.

T cells express distinctive membrane molecules. Included among these are the T cell antigen receptor (TCR), which appears on the cell surface in association with CD3; and accessory molecules such as CD5, CD28 and CD45R. Subpopulations of T cells can be distinguished by the presence of additional membrane molecules. Thus, for example, T cells that express CD4 recognize antigen associated with class II MHC molecules and generally function as helper cells, while T cells that express CD8 recognize antigen associated with class I MHC molecules and generally function as cytotoxic cells. The $CD4^+$ subpopulation of T cells can be categorized fturther into at least two subsets on the basis of the types of cytokines secreted by the cell. Thus, while both subsets secrete IL-3 and GM-CSF, TH1 cells generally secrete IL-2, IFN-$\gamma$, and TNF-$\alpha$, whereas TH2 cells generally secrete IL-4, IL-5, IL-10, and IL-13.

Minor changes in the peptide bound to the MHC molecule can not affect the affinity of the peptide-MHC molecule interaction, yet they can generate partial signals that lead to a halfway response characterized by proliferation and secretion of only a fraction of the cytokines produced during a full T cell response. Some modified peptides can even block proliferation and cytokine secretion altogether and induce a state of T cell anergy or unresponsiveness. There are thus three different types of peptides: agonist (those that stimulate a full response), partial agonist (those that stimulate a partial response) and antagonist (those that induce unresponsiveness). When a single APC presents a mixture of an agonist and an antagonist on its surface, the negative effect of the latter can overcome the positive effect of the former, even if the antagonist is present in much smaller amounts than the agonist. Some viruses seem to use mutations in their proteins to produce antagonist peptides capable of suppressing the activity of the T cell clones that recognize agonist peptides derived from the original wild-type virus.

Secretion by a T cell of a particular cytokine is generally associated with a particular function. For example, differences in the cytokines secreted by the TH1 and TH2 subsets of $CD4^+$ T cells are believed to reflect different biological functions of these two subsets. The TH1 subset is responsible for classical cell-mediated functions such as delayed-type hypersensitivity and activation of cytotoxic T cells, whereas the TH2 subset functions more effectively as a helper for B-cell activation. The TH1 subset can be particularly suited to respond to viral infections and intracellular pathogens because it secretes IL-2 and IFN-$\gamma$, which activate cytotoxic T cells. The TH2 subset can be more suited to respond to extracellular bacteria and helminthic parasites and can mediate allergic reactions, since IL-4 and IL-5 are known to induce IgE production and eosinophil activation, respectively. There is also considerable evidence suggesting that preferential activation of TH1 cells plays a central role in the pathogenesis of a number of autoimmune diseases. Secretion of IL-10 by TH2 cells is thought to suppress, in an indirect manner, cytokine production by TH1 cells, and, accordingly, has a general immunosuppressive effect. A shift in the TH1/TH2 balance can result in an allergic response, for example, or, in an increased cytotoxic T cell response.

The changes initiated by the TCR in the first few minutes to hours of activation lead to transition of the cell from the G0 to G1 phase of the cell cycle. Several hours after stimulation of the T cell begins to express IL-2 and high-affinity IL-2 receptor. IL2 gene expression is effected by a set of transcription factors that are activated by the converging signaling pathways triggered by the ligation of TCR, CD28 and possibly other T cell surface molecules.

The transcription factors also induce expression of the CD25 gene, which encodes the $\alpha$-subunit of the high-affinity IL-2 receptor. The interaction of IL-2 with the high-affinity receptor initiates signaling pathways that cause the T cell to transit from the G1 to the S phase of the cell cycle and progress to cell division. The signaling pathways control the expression and activity of several key proteins necessary for cell division. Some of these are also activated directly by TCR- and CD28-dependent signals while others are energized only by signals provided via the IL-2 receptor.

The stimulated T cell undergoes a sequence of phenotypic changes beginning with its progression from the resting state to mitosis and later to differentiation into effector and memory cells. Among the earliest (immediate) changes, observable within 15–30 minutes of stimulation, are the expression of genes encoding transcription factors such as c-Fos, NF-AT, c-Myc and NF-$\kappa$B, protein kinases such as Jak-3 and protein phosphatases such as Pac-1. The subsequent early changes, occurring within several hours of stimulation, mark the beginning of the expression of genes encoding activation antigens. These include several cytokines (IL-2 and others), IL-2 receptor subunit $\alpha$ (CD25), insulin receptor, transferrin receptor and several other surface molecules such as CD 26, CD30, CD54, CD69 and CD70.

Activation antigens reach a maximum level of expression just before the first division, 24 hours after stimulation. During this period the level of expression of several other molecules already expressed on resting T cells increases. At a later point, some days after activation commenced, late activation antigens become expressed on the T cells. These include MHC class II molecules and several members of the $\beta 1$ integrin family. Expression of late activation antigens marks the differentiation of the activated cell into effector or memory T cells.

T cells play important roles in autoimmunity, inflamation, cytotoxicity, graft rejection, allergy, delayed-type hypersensitivity, IgE-mediated hypersensitivity, and modulation of the humoral response. Disease states can result from the activation of self-reactive T cells, from the activation of T cells that provoke allergic reactions, or from the activation of autoreactive T cells following certain bacterial and parasitic infections, which can produce antigens that mimic human protein, rendering these protein "autoantigens." These diseases include, for example, the autoimmune diseases, autoimmune disorders that occur as a secondary event to infection with certain bacteria or parasites, T cell-mediated allergies, and certain skin diseases such as psoriasis and vasculitis. Furthermore, undesired rejection of a foreign antigen can result in graft rejection or even infertility, and such rejection can be due to activation of specific T lymphocyte populations. Pathological conditions can also arise from an inadequate T cell response to a tumor or a viral infection. In these cases, it would be desirable to increase an antigen-specific T cell response in order to reduce or eliminate the tumor or to eradicate an infection.

Autoimmune diseases have a variety of causes. For instance, autoimmune reactions can be provoked by injury or immunization with collagen, by superantigens, by genetic factors, or errors in immune regulation. Superantigens are polyclonal activators that can, among other things, stimulate clones previously anergized by an encounter with an autoantigen or clones that ignored the potential autoantigens because of their low expression or availability. Certain autoimmune disease are caused mainly by autoantibodies, others are T cell-mediated. Autoreactive T cells cause tissue damage in a number of autoimmune diseases including rheumatoid arthritis and multiple sclerosis.

In the treatment of autoimmune disorders, nonspecific immune suppressive agents have been used to slow the disease; these therapies often cause a general immunosuppression by randomly killing or inhibiting immunocompetent cells. Attempts to treat autoimmune disorders by modulating the activity of autoreactive T cells have included immunization with TCR peptides, treatment with interferon-$\beta$ (IFN-$\beta$) and T lymphocyte vaccination. Ebers (1994) *Lancet* 343:275–278; Hohlfeld (1997) *Brain* 120:865–916; and Hafler et al. (1992) *Clin. Immunol. Immunopathol.* 62:307–313.

The development of allergic sensitization, contact sensitivity and inflammation is dependent on activation and stimulation of T cells that exhibit pro-allergic functions. Allergen-specific T cells are believed to play an important role in the pathophysiology of atopic allergies. Elimination or suppression of allergen-specific T cells could help ameliorate allergic diseases caused by such T cells.

In the initial phase of an allergic reaction, antigen (allergen) enters the body, is picked up by APCs, displayed by them in the context of class II MHC molecules and recognized by helper T cell precursors. These are stimulated to proliferate and differentiate mainly into TH2 cells, which help B lymphocytes differentiate into antibody-producing plasma cells. As in any other antibody-mediated response, the B cells that receive specific help from TH cells are those that recognized the allergen via their surface receptors. Some of the cytokines produced by the TH2 cells, especially IL-4 and IL-13, stimulate the B cells to effect an immunoglobulin isotype switch and to produce IgE antibodies. The antibodies bind to high-affinity Fc receptors on the surface of mast cells in the connective tissue and mucosa, as well as to those on the surface of basophils in the circulation and mucosa and initiate the manifestations of allergic reaction.

Allograft rejection is caused principally by a cell-mediated immune response to alloantigens (primarily MHC molecules) expressed on cells of the graft. Analysis of the T lymphocyte subpopulations involved in allograft rejection has implicated both $CD4^+$ and $CD8^+$ populations. TH1 cells initiate the inflammatory reaction of delayed-type hypersensitivity, leading to the recruitment of monocytes and macrophages into the graft. Natural kill (NK) cells, presumably alerted by the absence in the graft of MHC molecules present in the recipient, can also attack the graft in the early phases of the response. Neutrophils are mainly responsible for clearing the wound or removing damaged cells and cellular debris in the late phase of the allograft reaction.

Most immunosuppressive treatments developed have the disadvantage of being non-specific; that is, they result in generalized immunosuppression, which places the recipient at increased risk for infection. Immunosuppressive agents employed to prevent organ rejection include mitotic inhibitors such as azathioprine, cyclophosphamide and methotrexate; corticosteroids; and drugs, such as cyclosporin, FK506 and rapamycin, which inhibit the transcription of the genes encoding IL-2 and the high-affinity receptor for IL-2.

In the treatment of cancers, cellular immunotherapy has been employed as an alternative, or an adjunct to, conventional therapies such as chemotherapy and radiation therapy. For example, cytotoxic T lymphocyte (CTL) responses can be directed against antigens specifically or preferentially presented by tumor cells. Following activation with T cell cytokines in the presence of appropriately presented tumor antigen, tumor infiltrating lymphocytes (TILs) proliferate in culture and acquire potent anti-tumor cytolytic properties. Weidmann et al. (1994) Cancer *Immunol. Immunother.* 39:1–14.

The introduction into a cancer patient of in vitro activated lymphocyte populations has yielded some success. Adoptive immunotherapy, the infusion of immunologically active cells into a cancer patient in order to effect tumor regression, has been an attractive approach to cancer therapy for several decades. Two general approaches have been pursued. In the first, donor cells are collected that are either naturally reactive against the host's tumor, based on differences in the expression of histocompatibility antigens, or made to be reactive using a variety of "immunizing" techniques. These activated donor cells are then transfused to a tumor-bearing host. In the second general approach, lymphocytes from a cancer patient are collected, activated ex vivo against the tumor and then reinfused into the patient. Triozzi (1993) *Stem Cells* 11:204–211; and Sussman et al. (1994) *Annals Surg Oncol.* 1:296.

Current methods of cancer treatment are relatively nonselective. Surgery removes the diseased tissue, radiotherapy shrinks solid tumors and chemotherapy kills rapidly dividing cells. Systemic delivery of chemotherapeutic agents, in particular, results in numerous side effects, in some cases severe enough to preclude the use of potentially effective drugs.

Viral diseases are also candidates for immunotherapy. Heslop et al. (1996) *Nature Med.* 2:551–555. Immunological responses to viral pathogens are sometimes ineffective in eradicating or sufficiently depleting the virus. Furthermore, the highly mutable nature of certain viruses, such as human immunodeficiency virus, allows them to evade the immune system.

Clearly, there is a need to identify, analyze and enrich populations of T cells involved in the above-mentioned pathologies. Currently, several methods for analysis and for enrichment of antigen-specific and/or cytokine-secreting T cells exist. Enrichment of antigen-specific T cells can be achieved using selective culturing techniques to obtain T cell lines and T cell clones. These techniques generally involve culturing the T cells in vitro over a period of several weeks and using rather cumbersome methods to select lines or clones exhibiting the desired phenotype, such as cytokine secretion. Other attempts to detect and enrich for antigen-specific T cells have employed defined multimeric MHC-antigen and MHC-peptide complexes. U.S. Pat. No. 5,635,363. For such a technique to be successful, however, MHC-antigen complexes of the correct MHC allotype are required, and the selection is limited to antigen specificity, i.e., no selection for cytokine secretion is afforded by this technique.

Intracellular cytokine staining after antigen activation, followed by FACS analysis, is the method used to obtain information regarding the antigen specificity and kinetics of cytokine production. Waldrop et al. (1997) *J. Clin. Invest.* 99:1739–1750. This method is useful for analysis only, since the cells are not viable after this procedure. Similarly, cytokine ELISPOT assays are useful for analysis only. Miyahira et al. (1995) *J. Immunol. Met.* 181:45–54; and Lalvani et al. (1997) *J. Exp. Med.* 186:859–865. In these assays, secreted cytokines are trapped in a surrounding matrix for analysis, but there is no mechanism for identifying and retrieving the cell which secreted the cytokine. The gel microdrop technology is not suited to processing large numbers of cells such as would be necessary for treatment of the above-mentioned indications.

It is apparent from the foregoing discussion that there is a need for reliable techniques for analyzing and separating populations of T cells, based on secreted product, for a number of therapeutic and diagnostic purposes. The present invention addresses this need by providing methods for analyzing, separating and enriching populations of antigen-specific T cells.

DISCLOSURE OF THE INVENTION

The invention provides a method for convenient analysis and cell separation of antigen-specific T cells based on one or more products secreted by these cells in response to antigen stimulation. The T cells are provided with a capture moiety specific for the product (or, "specific binding partner"), which can then be used directly as a label. The binding of the product to the capture moiety results in a "captured product." Alternatively, the cells are bound to the product via the capture moiety and can be further labeled via label moieties that bind specifically to the product and that are, in turn, labeled either directly or indirectly with traditional labeling materials such as fluorophores, radioactive isotopes, chromophores or magnetic particles.

The labeled cells can then be separated using standard cell sorting techniques based on these labels. Such techniques include, but are not limited to, flow cytometry, FACS, high gradient magnetic gradient separation, centrifugation.

Thus, in one aspect, the invention encompasses a method to stimulate and separate antigen-specific T cells from a population of cells according to a product secreted and released by the antigen specific T cells in response to the stimulation. The method comprises stimulating a mixture of cells containing T cells with antigen, and effecting a separation of antigen-stimulated cells according to the degree to which they are labeled with the product. Antigen stimulation is achieved by exposing the cells to at least one antigen under conditions effective to elicit antigen-specific stimulation of at least one T cell. Labeling with the product is achieved by modifying the surface of the cells to contain at least one capture moiety, culturing the cells under conditions in which the product is secreted, released and specifically bound ("captured" or "entrapped") to said capture moiety; and labeling the captured product with a label moiety, where the labeled cells are not lysed as part of the labeling procedure or as part of the separation procedure.

Another aspect of the invention is a composition of matter containing antigen-specific T cells capable of capturing a product secreted and released by these cells in response to antigen stimulation, where the surface of the cells is modified to contain a capture moiety for the product. The captured product can be separately labeled by a label moiety.

Still another aspect of the invention is antigen-specific T cells and progeny thereof separated by the above-described method.

Yet another aspect of the invention is a method to label antigen-specific T cells with a product secreted and released by the cells in response to antigen stimulation, by modifying the surface of these cells to contain a specific binding partner for the product coupled to the cell surface, and culturing the cells under conditions wherein the product is secreted and released.

An additional aspect of the invention is a method of analyzing a population of antigen-specific T cells to determine the proportion of cells that secrete an amount of product relative to other cells in the population, where the product is secreted in response to antigen stimulation. The method comprises labeling the cells by the above-described method, further labeling the cells with a second label that does not label the captured product, and detecting the amount of product label relative to the second cell label. Such methods are useful, for example, in assessing the immune status of an individual.

A further aspect of the invention is methods for use of T cell populations enriched in antigen-specific T cells. The methods comprise administering to an individual in need of treatment a composition comprising a T cell population enriched in antigen-specific T cells. Such methods are useful to treat a variety of pathological conditions, including cancer, allergies, immunodeficiencies, autoimmune disorders, and viral diseases.

Yet another aspect of the invention is a kit for use in separation of antigen-specific T cells from a mixed population comprising effector cells. The kit can contain a physiologically acceptable medium which can be of varying degrees of viscosity up to a gel-like consistency, a product capture system comprising anchor and capture moieties; a label system for detecting the captured product; and instructions for use of the reagents, all packaged in appropriate containers. Optionally, the kit further comprises a magnetic labeling system and/or one or more biological modifiers.

Still another aspect of the invention is a kit for use in the detection/separation of antigen-specific T cells that secrete a desired product in response to antigen stimulation, the kit comprising a product capture system comprising anchor and capture moieties; a label system for detecting the captured product; and instructions for use of the reagents, all packaged in appropriate containers. Optionally, the kit further comprises a magnetic labeling system, and/or antigen, and/or one or more biological modifiers.

BRIEF DESCRIPTION OF THE DRAWINGS

FIG. 6 is a series of dot plots depicting the isolation and detection of TT-specific IL-4-secreting $CD4^+$ T cells. Dot plots show CD4-Cy5 vs. anti IL-4-PE staining of PBMC from healthy adult donors stimulated with (A,C) or without (B,D) magnetic enrichment of IL-4-secreting cells. Live lymphocytes were gated according to light-scatter properties and propidium iodide exclusion.

MODES FOR CARRYING OUT THE INVENTION

Figure 1A:
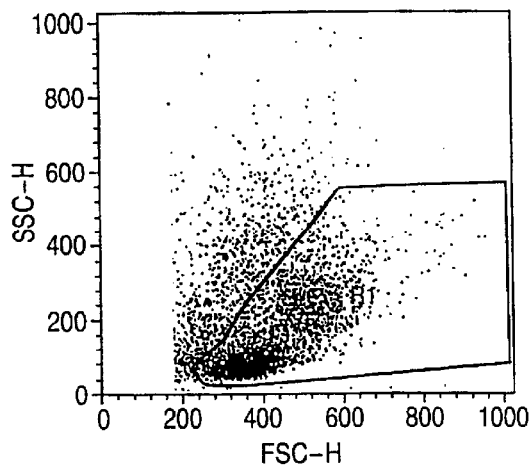
FIGS. 1A–P are FACS plots showing analysis of cells subjected to the separation protocol described in Example 1. A–H show analysis of control cells cultured with no peptide; I–P show analysis of peptide-stimulated cells. A, C, I, and K show scatter properties of the starting cell population (A and I) and the enriched cell population (C and K). B, D, J. and L show profiles of PI versus PE staining of the starting cell population (B and J) and the enriched cell population (D and L). Plots E–H and M–P show FITC-labeled anti-CD8 versus PE-labeled anti-IFN-γ staining of the starting cell population (E and M), the first negative population (F and N), the second negative population (G and O) and the enriched cell population (H and P).
Figure 1B:
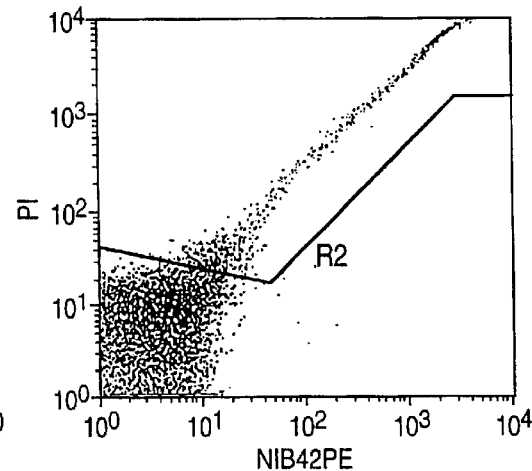
Figure 1C:
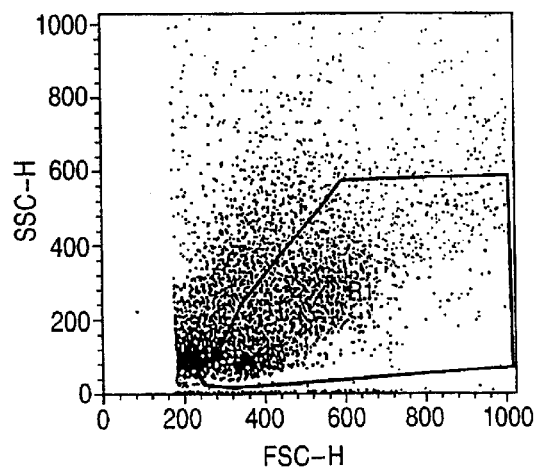
Figure 1D:
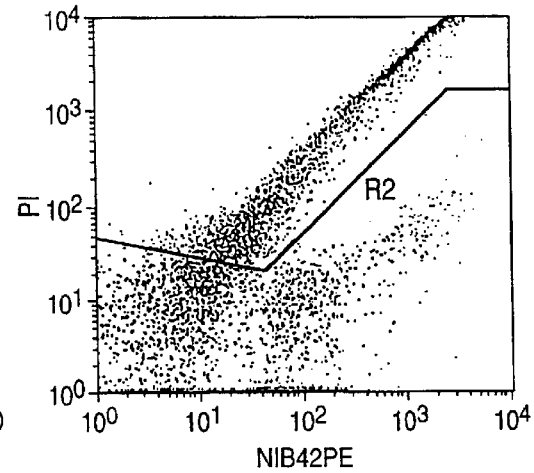
Figure 1E:
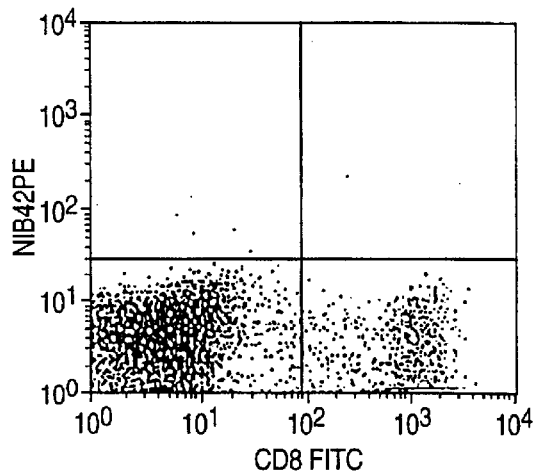
Figure 1F:
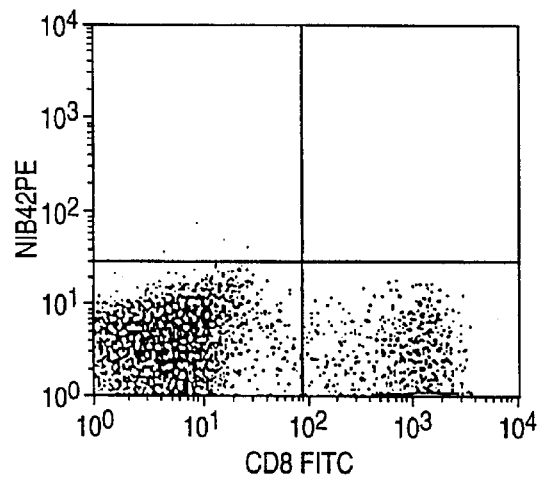
Figure 1G:
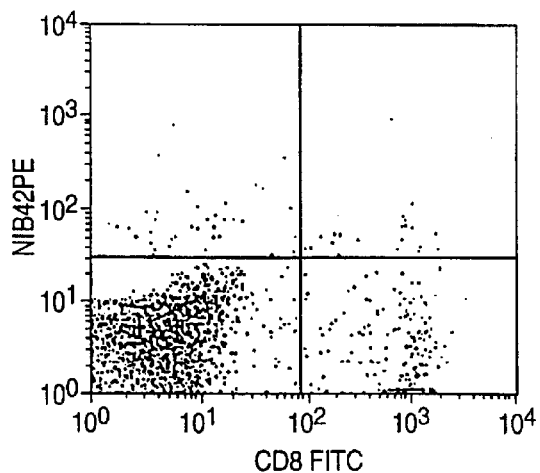

The present invention provides methods for detecting, analyzing and separating antigen-stimulated T cells on the basis of secreted product, where the product is secreted as a result of antigen stimulation. The methods are based on capture and relocation to the cell surface of the secreted product.

The captured product permits the cell to be detected, analyzed and, if desired, sorted, according to the presence, absence or amount of the product present. The means of capture comprises a product-specific binding partner ("capture moiety") anchored to the cell surface by a means suitable for the cell to be sorted.

The approach presented here combines, inter alia, the following advantages: (a) it permits rapid isolation, enumeration, phenotyping and expansion of live antigen-specific T lymphocytes without the need of cyclical activation of T cells with antigen and APCs; (b) it is generally applicable for isolation of T cells reactive to APCs that have been pulsed with synthetic peptides, native proteins, cell extracts, nonviable pathogens, transduced with retroviral vectors, infected with recombinant viral vectors, transfected with RNA or DNA, etc.; (c) it can be used for the isolation of both $CD4^+$ antigen-specific Th cells and $CD8^+$ antigen-specific CTLs; and (d) it enables selective isolation of antigen specific T cells with particular cytokine-mediated effector functions, e.g., of antigen-specific Th1-, Th2-, or Th3-like lymphocytes.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodic updates); "PCR: The Polymerase Chain Reaction", (Mullis et al., eds., 1994); and "Current Protocols in Immunology" (J. E. Coligan et al., eds., 1991).

Cell sorting and cell analysis methods are known in the art and are described in, for example, *The Handbook of Experimental Immunology*, Volumes 1 to 4, (D. N. Weir, editor) and *Flow Cytometry and Cell Sorting* (A. Radbruch, editor, Springer Verlag, 1992).

As used herein, a "specific binding partner" or "capture moiety" intends a member of a pair of molecules (a "specific binding pair") that interact by means of specific non-covalent interactions that depend on the three-dimensional structures of the molecules involved. A "label moiety" is a detectable, either directly or indirectly. When the capture moiety is an antibody, it can be referred to as the "capture antibody" or "catch antibody." The capture moieties are those which attach both to the cell, either directly or indirectly, and the product. The label moieties are those which attach to the product and can be directly or indirectly labeled.

As used herein, the term "antibody" is intended to include polyclonal and monoclonal antibodies, chimeric antibodies, haptens and antibody fragments, and molecules which are antibody equivalents in that they specifically bind to an epitope on the product antigen. The term "antibody" includes polyclonal and monoclonal antibodies of any isotype (IgA, IgG, IgE, IgD, IgM), or an antigen-binding portion thereof, including, but not limited to, F(ab) and Fv fragments such as sc Fv, single chain antibodies, chimeric antibodies, humanized antibodies, and a Fab expression library. Antibodies can also be immobilized for instance on a polymer or a particle.

"Bispecific antibody" and "bispecific antibodies," also known as bifunctional antibodies, intends antibodies that recognize two different antigens by virtue of possessing at least one first antigen combining site specific for a first antigen or hapten, and at least one second antigen combining site specific for a second antigen or hapten. Such antibodies can be produced by recombinant DNA methods or include, but are not limited to, antibodies chemically by methods known in the art. Chemically created bispecific antibodies that have been reduced and reformed so as to retain their bivalent characteristics and antibodies that have been chemically coupled so that they have at least two antigen recognition sites for each antigen. Bispecific antibodies include all antibodies or conjugates of antibodies, or polymeric forms of antibodies which are capable of recognizing two different antigens. The label moiety can be a fluorochromated antiproduct antibody, which can include, but is not limited to, magnetic bead conjugated, colloidal bead conjugated, FITC, Phycoerythrin, PerCP, AMCA, fluorescent particle or liposome conjugated antibodies. Alternatively the label moiety can be any suitable label including but not limited to those described herein. Bispecific antibodies include antibodies that have been reduced and reformed so as to retain their bivalent characteristics and to antibodies that have been chemically coupled so that they can have several antigen recognition sites for each antigen.

As used herein the term "effector cell population" intends a cell population which comprises at least one T cell. An effector cell population can be obtained from a starting cell population from which antigen-specific T cells are enriched.

The terms "cell," and "cells," and "cell population," used inter-changeably, intend one or more mammalian cells. The term includes progeny of a cell or cell population. Those skilled in the art will recognize that "cells" include progeny of a single cell, and the progeny can not necessarily be completely identical (in morphology or of total DNA complement) to the original parent cell due to natural, accidental, or deliberate mutation and/or change.

The terms "T lymphocyte," "T cell," "T cells," and "T cell population," used interchangeably, intends a cell or cells which display on their surface one or more antigens characteristic of T cells, such as, for example, CD2 and CD3. The term includes progeny of a T cell or T cell population. A "T lymphocyte" or "T cell" is a cell which expresses CD3 on its cell surface and a T cell antigen receptor (TCR) capable of recognizing antigen when displayed on the surface of autologous cells, or any antigen-presenting matrix, together with one or more MHC molecules or, one or more non-classical MHC molecules. The term "T cells" as used herein denotes any T cells known in the art, for instance, lymphocytes that are phenotypically CD3$^+$, i.e., express CD3 on the cell surface, typically detected using an anti-CD3 monoclonal antibody in combination with a suitable labeling technique. The T cells enriched by the methods of this invention are generally CD3$^+$. The T cells enriched by the methods of this invention are also generally, although not necessarily, positive for CD4, CD8, or both.

The term "substantially enriched" as used herein, indicates that a cell population is at least about 50-fold, more preferably at least about 500-fold, and even more preferably at least about 5000-fold or more enriched from an original mixed cell population comprising the desired cell population.

The term "antigen-presenting matrix," as used herein, intends a molecule or molecules which can present antigen in such a way that the antigen can be bound by a T cell antigen receptor on the surface of a T cell. An antigen-presenting matrix can be on the surface of an antigen-presenting cell (APC), on a vesicle preparation of an APC, or can be in the form of a synthetic matrix on a bead or a plate. The term "antigen presenting cell", as used herein, intends any cell which presents on its surface an antigen in association with a MHC or portion thereof, or, one or more non-classical MHC molecules, or a portion thereof.

The term "autogeneic," "autologous," or, "self," as used herein, indicates the origin of a cell. Thus, a cell is autogeneic if the cell was derived from an individual (the "donor") or a genetically identical individual and is to be readministered to the individual. An autogeneic cell can also be a progeny of an autogeneic cell. The term also indicates that cells of different cell types are derived from the same donor or genetically identical donors. Thus, an effector cell and an antigen presenting cell are said to be autogeneic if they were derived from the same donor or from an individual genetically identical to the donor, or if they are progeny of cells derived from the same donor or from an individual genetically identical to the donor.

Similarly, the term "allogeneic," or "non-self," as used herein, indicates the origin of a cell. Thus, a cell and progeny thereof is allogeneic if the cell was derived from an individual not genetically identical to the recipient to whom it is administered; in particular, the term relates to non-identity in expressed MHC molecules. The term also indicates that cells of different cell types are derived from genetically non-identical donors, or if they are progeny of cells derived from genetically non-identical donors. For example, an APC is said to be allogeneic to an effector cell if they are derived from genetically non-identical donors.

A "disease or condition related to a population of antigen-specific T cells" is one which can be related to a population of antigen-specific T cells or lack of adequate numbers thereof, and includes, for example, autoimmune diseases in which antigen-specific T cells are primarily responsible for the pathogenesis of the disease; cancers, in which cancerous cell growth is not adequately controlled by tumor-specific cytotoxic T cells; viral diseases, in which virus-infected cells are not lysed by cytotoxic T cells; allergies, in which T cells specific for allergens mediate undesired effects; immunodeficiencies, in which inadequate numbers of T cells are present in an individual due to either infection (such as HIV) or congenitally (such as DiGeorge syndrome). It is also one in which antigen-specific T cells modulate or regulate the activity of another cell or cell population which is primarily responsible for a disease state; it is also one in which the presence of a population of antigen-specific T cells is not the primary cause of the disease, but which plays a key role in the pathogenesis of the disease; it is also one in which a population of antigen-specific T cells mediates an undesired rejection of a foreign antigen.

An "individual" is a vertebrate, preferably a mammal, more preferably a human. Mammals include, but are not limited to, humans, farm animals, sport animals, and pets.

An "effective amount" is an amount sufficient to effect beneficial or desired clinical results. An effective amount can be administered in one or more administrations. For purposes of this invention, an effective amount of antigen-specific T cells is an amount that is sufficient to diagnose, palliate, ameliorate, stabilize, reverse, slow or delay the progression of the disease state.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to not administering enriched T cell populations of the present invention.

The present invention provides methods for obtaining a cell population enriched in antigen-specific T cells which secrete a product, where the product is secreted as a result of antigen stimulation. The methods generally involve obtaining a mixed population of cells comprising T cells; exposing the cell population to at least one antigen under conditions effective to elicit antigen-specific stimulation of at least one T cell; modifying the surface of said mixed population to contain attached thereto a specific binding partner for the product; allowing expression of at least one product by the stimulated T cells, wherein the product is secreted in response to the stimulation; allowing binding of the product to a capture moiety coupled to the surface of the cell to form a cell bound capture moiety-product complex, thereby labeling the cells; and separating the stimulated T cells according to the degree to which they are labeled with said product.

Of course, modification of the cell surface with a specific binding partner can be carried out before, during, or after antigen stimulation.

Antigen Presenting Matrices and Effector Cell Populations

The present invention provides methods for obtaining a cell population enriched in antigen-specific T cells which secrete a product in response to antigen stimulation. The methods comprise obtaining a mixed population of cells (i.e., an "effector cell population"), and exposing the cell population to at least one antigen. The mixed cell population can be obtained by any method known in the art and is preferably enriched for T cells. Exposure to antigen can be achieved using antigen-presenting matrices, which can be on the surface of antigen-presenting cells (APC's). Antigen-presenting matrices and effector cells can be obtained from a variety of sources. The mixed population of cells can be stimulated by antigen in vitro or in vivo, or modified in any of a variety of ways, for example, chemically or genetically modified.

Antigen Presenting Matrices

The T cell populations which are subjected to the methods of the present invention are exposed to at least one antigen under conditions effective to elicit antigen-specific stimulation. A T cell which is stimulated by the at least one antigen. is said to be antigen specific, i.e., it displays on its cell surface an antigen receptor which specifically recognizes and binds to an antigen in association with a molecule capable of presenting antigen, such as a classical or non-classical MHC molecule or a portion thereof, on an antigen-presenting matrix, for example, a synthetic antigen-presenting matrix or one that is present on the surface of an APC.

The antigen-presenting molecule can be an MHC molecule, which can be class I or class II or, a non-classical MHC molecule such as CD1; an MHC epitope; a fusion protein comprising an MHC epitope; or a synthetic MHC epitope. The nature of the antigen-presenting molecule is not critical, so long as it is capable of presenting antigen to an effector cell. Methods of preparing MHC epitopes are known in the art.

Antigen-presenting matrices include those on the surface of an APC as well as synthetic antigen-presenting matrices. APCs suitable for use in the present invention are capable of presenting exogenous peptide or protein or endogenous antigen to T cells in association with an antigen-presenting molecule, such as an MHC molecule. APCs include, but are not limited to, macrophages, dendritic cells, CD40-activated B cells, antigen-specific B cells, tumor cells, virus-infected cells and genetically modified cells.

APCs can be obtained from a variety of sources, including but not limited to, peripheral blood mononuclear cells (PBMC), whole blood or fractions thereof containing mixed populations, spleen cells, bone marrow cells, tumor infiltrating lymphocytes, cells obtained by leukapheresis, lymph nodes, e.g., lymph nodes draining from a tumor. Suitable donors include an immunized donor, a non-immunized (naïve) donor, treated or untreated donors. A "treated" donor is one that has been exposed to one or more biological modifiers. An "untreated" donor has not been exposed to one or more biological modifiers. APC's can also be treated in vitro with one or more biological modifiers.

The APCs are generally alive but can also be irradiated, mitomycin C treated, attenuated, or chemically fixed. Further, the APCs need not be whole cells. Instead, vesicle preparations of APCs can be used.

APCs can be genetically modified, i.e., transfected with a recombinant polynucleotide construct such that they express a polypeptide or an RNA molecule which they would not normally express or would normally express at lower levels. Examples of polynucleotides include, but are not limited to, those which encode an MHC molecule; a co-stimulatory molecule such as B7; or an antigen. For example, expression of a polynucleotide encoding an MHC molecule under transcriptional control of a strong promoter such as the CMV promoter, can result in high level expression of the MHC molecule on the cell surface, thus increasing the density of antigen presentation. Alternatively, an APC can be transfected with a polynucleotide construct comprising a polynucleotide encoding an antigen under transcriptional control of a strong promoter such as the CMV promoter such that the antigen is expressed on the cell surface together with an MHC molecule.

The nucleotide sequence encoding a polypeptide is operably linked to control sequences for transcription and translation. A control sequence is "operably linked" to a coding sequence if the control sequence regulates transcription or translation. Any method in the art can be used for the transformation, or insertion, of an exogenous polynucleotide into an APC, for example, lipofection, transduction, infection or electroporation, using either purified DNA, viral vectors, or DNA or RNA viruses. The exogenous polynucleotide can be maintained as a non-integrated vector, for example, a plasmid, or, can be integrated into the host cell genome.

Cells which do not normally function in vivo in mammals as APCs can be modified to function as APCs. A wide variety of cells can function as APCs when appropriately modified. Examples of such cells are insect cells, for example Drosophila or Spodoptera; foster cells, such as the hunan cell line T2, which bears a mutation in its antigen presenting pathway that restricts the association of endogenous peptides with cell surface MHC class I molecules. Zweerink et al. (1993) *J. Immunol.* 150:1763–1771. For example, expression vectors which direct the synthesis of one or more antigen-presenting polypeptides, such as MHC molecules, and, optionally, accessory molecules such as B7, can be introduced into these cells to effect the expression on the surface of these cells antigen presentation molecules and, optionally, accessory molecules or functional portions thereof. Alternatively, antigen-presenting polypeptides and accessory molecules which can insert themselves into the cell membrane can be used. For example, glycosyl-phosphotidylinositol (GPI)-modified polypeptides can insert themselves into the membranes of cells. Medof et al. *J. Exp. Med.* 160:1558–1578; and Huang et al. *Immunity* 1:607–613. Accessory molecules include, but are not limited to, co-stimulatory antibodies such as antibodies specific for CD28, CD80, or CD86; costimulatory molecules, including, but not limited to, B7.1 and B7.2; adhesion molecules such as ICAM-1 and LFA-3; and survival molecules such as Fas ligand and CD70. See, for example, PCT Publication No. WO 97/46256.

Alternatively, a synthetic antigen-presenting matrix can be used to present antigen to effector cells. A synthetic matrix can include an antigen presenting molecule, preferably an MHC Class I or MHC Class II molecule, immobilized on a solid support, for example, beads or plates. Accessory molecules can be present, which can be co-immobilized or soluble, the molecules including, but not limited to, co-stimulatory antibodies such as antibodies specific for CD28, CD80, or CD86; costimulatory molecules, including, but not limited to, B7.1 and B7.2; adhesion molecules such as ICAM-1 and LFA-3; and survival molecules such as Fas ligand and CD70. Portions of accessory molecules can also be used, as long as their function is maintained. Solid supports include metals or plastics, porous materials, microbeads, microtiter plates, red blood cells, and liposomes. See, for example, PCT Publication No. WO 97/46256; and WO 97/35035.

Methods for determining whether an antigen-presenting matrix, whether it is on a cell surface or on a synthetic support, is capable of presenting antigen to an effector cell, are known in the art and include, for example, $^3$H-thymidine uptake by effector cells, cytokine production by effector cells, and cytolytic $^{51}$Cr-release assays.

Effector Cell Populations

Antigen-specific T cells can be isolated from an effector cell population, i.e., a population of hematopoietic cells, preferably enriched for T cells. The effector cell population is a starting population from which antigen-specific T cells are isolated.

An effector cell population suitable for use in the present invention can be autogeneic or allogeneic, preferably autogeneic. When effector cells are allogeneic, preferably the cells are depleted of alloreactive cells before use. This can be accomplished by any known means, including, for example, mixing the allogeneic effector cells and a recipient cell population and incubating them for a suitable time, then depleting CD69$^+$cells, or inactivating alloreactive cells, or inducing anergy in the alloreactive cell population.

The effector cell population can comprise unseparated cells, i.e., a mixed population, for example, a PBMC population, whole blood, and the like. The effector cell population can be manipulated by positive selection based on expression of cell surface markers, negative selection based on expression of cell surface markers, stimulation with one or more antigens in vitro or in vivo, treatment with one or more biological modifiers in vitro or in vivo, subtractive stimulation with one or more antigens or biological modifiers, or a combination of any or all of these.

Effector cells can be obtained from a variety of sources, including but not limited to, PBMC, whole blood or fractions thereof containing mixed populations, spleen cells, bone marrow cells, tumor infiltrating lymphocytes, cells obtained by leukapheresis, biopsy tissue, lymph nodes, e.g., lymph nodes draining from a tumor. Suitable donors include an immunized donor, a non-immunized (naïve) donor, treated or untreated donors. A "treated" donor is one that has been exposed to one or more biological modifiers. An "untreated" donor has not been exposed to one or more biological modifiers.

Methods of extracting and culturing effector cells are well known. For example, effector cells can be obtained by leukapheresis, mechanical apheresis using a continuous flow cell separator. For example, lymphocytes and monocytes can be isolated from the buffy coat by any known method, including, but not limited to, separation over Ficoll-Hypaque™ gradient, separation over a Percoll gradient, or elutriation. The concentration of Ficoll-Hypaque™ can be adjusted to obtain the desired population, for example, a population enriched in T cells. Other methods based on cell-specific affinity columns are known and can be used. These include, for example, fluorescence-activated cell sorting (FACS), cell adhesion, magnetic bead separation, and the like. Affinity-based methods can utilize antibodies, or portions thereof, which are specific for cell-surface markers and which are available from a variety of commercial sources, including, the American Type Culture Collection (Rockville, Md.). Affinity-based methods can alternatively utilize ligands or ligand analogs, of cell surface receptors.

The effector cell population can be subjected to one or more separation protocols based on the expression of cell surface markers. For example, the cells can be subjected to positive selection on the basis of expression of one or more cell surface polypeptides, including, but not limited to, "cluster of differentiation" cell surface markers such as CD2, CD3, CD4, CD8, TCR, CD45, CD45RO, CD45RA, CD11b, CD26, CD27, CD28, CD29, CD30, CD31, CD40L; other markers associated with lymphocyte activation, such as the lymphocyte activation gene 3 product (LAG3), signaling lymphocyte activation molecule (SLAM), T1/ST2; chemokine receptors such as CCR3, CCR4, CXCR3, CCR5; homing receptors such as CD62L, CD44, CLA, CD146, α4β7, αEβ7; activation markers such as CD25, CD69 and OX40; and lipoglycans presented by CD1. The effector cell population can be subjected to negative selection for depletion of non-T cells and/or particular T cell subsets. Negative selection can be performed on the basis of cell surface expression of a variety of molecules, including, but not limited to, B cell markers such as CD19, and CD20; monocyte marker CD14; the NK cell marker CD56.

The effector cell population can be manipulated by exposure, in vivo or in vitro, to one or more antigens. Antigens include, but are not limited to, peptides; proteins; glycoproteins; lipids; glycolipids; cells; cell extracts; tissue extracts; whole microorganisms such as protozoans, bacteria, and viruses. Antigens can be unmodified, i.e., used in their native state. Alternatively, an antigen can be modified by any known means, including, but not limited to, heating, for example to denature a protein or to inactivate a pathogen; chemical modification to denature a protein, or to cross-link two antigen molecules; glycosylation; chemical modification with moieties including, but not limited to polyethylene glycol; and enzymatic digestion. If more than one antigen is used, the exposure can be simultaneous or sequential.

The effector cells can be cultured in the presence of at least one antigen associated with a condition to be treated. The antigen can be a single antigen with multiple antigenic determinants or can be a mixture of antigens. The antigen can be an autoantigen or a foreign antigen, depending on the condition to be treated. Autoantigens include antigens associated with autoimmune diseases and those associated with cancer cells. The antigen can be a protein, cells, a tissue or a target organ. If the antigen is an autoantigen, the autoantigen can be part of an organ, for example the brain or the thyroid gland and need not be purified therefrom. Purified autoantigens or mixtures of purified autoantigens can also be used.

Co-culturing of peripheral blood leukocytes (PBL) or tumor infiltrating lymphocytes (TIL) with autologous tumor cells is generally accompanied by cytokine stimulation. Sporn et al.(1993) *Cancer Immunol. Immunother.* 37:175–180; and Peyret et al. (1991) *Chirurgie* 117:700–709.

An effector cell population can be manipulated by exposure, in vivo or in vitro, to one or more biological modifiers. Suitable biological modifiers include, but are not limited to, cytokines such as IL-2, IL-4, IL-10, TNF-α, IL-12, IFN-γ; non-specific modifiers such as phytohemagglutinin (PHA), phorbol esters such as phorbol myristate acetate (PMA), concanavalin-A, and ionomycin; antibodies specific for cell surface markers, such as anti-CD2, anti-CD3, anti-IL-2 receptor, anti-CD28; chemokines, including, for example, lymphotactin. The biological modifiers can be native factors obtained from natural sources, factors produced by recombinant DNA technology, chemically synthesized polypeptides or other molecules, or any derivative thereof having the functional activity of the native factor. If more than one biological modifier is used, the exposure can be simultaneous or sequential.

The present invention provides compositions comprising T cells enriched in antigen-specific cells, enriched according to the methods of the invention. By "enriched" is meant that a cell population is at least about 50-fold, more preferably at least about 500-fold, and even more preferably at least about 5000-fold or more enriched from an original mixed cell population comprising the desired cell population. The proportion of the enriched cell population which comprises the desired antigen-specific cells can vary substantially, from less than 10% up to 100% antigen-specific cells. The percentage which are antigen-specific can be readily determined, for example, by a $^3$H-thymidine uptake assay in which the T cell population is challenged by an antigen-presenting matrix presenting the desired antigen(s).

Cell Labeling

The methods herein are based on labeling the cells with a product secreted by the cells, where the product is secreted in response to antigen stimulation. To achieve labeling, the cell surface of a cell population is modified such that a moiety that binds specifically to a product, the "specific binding partner" is attached to the cell surface either directly or through an anchoring means (an "anchor moiety"), optionally through a linker to form a capture moiety. The cell population can contain numerous types of cells and generally made up of a mixed population. Preferably the cell population is hematopoietic, more preferably the cell population is effector cells, most preferably, the cell population is T cells or a subset thereof. Subsets can be isolated by virtue of cell surface markers, for instance, CD45 for lymphocytes, CD8 for cytotoxic cells, etc.

Products secreted in response to antigen stimulation are known in the art and include, but are not limited to, cytokines, such as IL-2, IL-4, IL-10, TNF-α, TGF-β and IFN-γ.

Specific binding partners include any moiety for which there is a relatively high affinity and specificity between product and binding partner, and in which the dissociation of the product:partner complex is relatively slow so that the product:partner complex is detected during the cell separation technique. Specific binding partners include, but are not limited to, substrates or substrate analogs to which a product will bind, peptides, polysaccharides, steroids, biotin, digitoxin, digitonin and derivatives thereof. In a preferred embodiment the specific binding partner is an antibody or antigen-binding fragment or derivative thereof. The term "antigen-binding fragment" includes any peptide that binds specifically to the product. Typically, these fragments include such immunoglobulin fragments as Fab, F(ab')$_2$, Fab', scFv (both monomer and polymeric forms) and isolated H and L chains. An antigen-binding fragment retains the specificity of the intact immunoglobulin, although avidity and/or affinity can be altered.

In the practice of the invention the capture moiety can be attached to a cell membrane (or cell wall) by a variety of methods. Suitable methods include, but are not limited to, direct chemical coupling to amino groups of the protein components, coupling to thiols (formed after reduction of disulfide bridges) of the protein components, indirect coupling through antibodies (including pairs of antibodies) or lectins, anchoring in the lipid bilayer by means of a hydrophobic anchor, and binding to the negatively charged cell surface by polycations.

In other embodiments, the capture moiety is introduced using two or more steps, e.g., by labeling the cells with at least one anchor moiety which allows the coupling of the capture moiety to the anchor moiety either directly, for instance by a biotin/avidin complex or indirectly, through a suitable linking moiety or moieties.

Suitable anchor moieties include lipophilic molecules such as fatty acids. Alternatively, antibodies or other specific binding agents to cell surface markers such as the MHC antigens or glycoproteins, can also be used.

The "capture moiety" can be coupled to the anchor moiety through a linking agent, and can also include a linker which multiplies the number of capture moieties available and thus the potential for capture of product, such as branched polymers, including, for example, modified dextran molecules, polyethylene glycol, polypropylene glycol, polyvinyl alcohol, and polyvinylpyrrolidone.

Methods for direct chemical coupling of antibodies to the cell surface are known in the art, and include, for example, coupling using glutaraldehyde or maleimide activated antibodies. Methods for chemical coupling using multiple step procedures include, but are not limited to, biotinylation, coupling of trinitrophenol (TNP) or digoxigenin using for example succinimide esters of these compounds. Biotinylation can be accomplished by, for example, the use of D-biotinyl-N-hydroxysuccinimide. Succinimide groups react effectively with amino groups at pH values above 7, and preferentially between about pH 8.0 and about pH 8.5. Biotinylation can be accomplished by, for example, treating the cells with dithiothreitol followed by the addition of biotin maleimide.

Coupling to the cells can also be accomplished using antibodies against cell surface antigens ("markers"). Antibodies directed to surface antigens generally require in the range of 0.1 to 1 µg of antibody per $10^7$ cells. However, this requirement will vary widely in response to the affinity of the antibody to the product and will need to be determined empirically. Such a determination is well within the skill of one in the art. Thus, the appropriate amount of antibody must be determined empirically and is within the skill of one in the art. This allows coupling to specific cells on cell type specific marker expression. For instance, classes of cells such as T cells or subsets thereof can be specifically labeled. As a capture moiety, a bispecific antibody can be used which has an antigen recognition site for the cell or an anchor moiety placed thereon, and the product.

A capture moiety, particularly capture antibodies should be selected based on the amount of secreted product. For example, for cells which secrete only a few molecules, a high affinity antibody will catch most of the secreted molecules. Alternatively, in the case where the cell secretes many molecules during the incubation time, a lower affinity antibody can be preferred to prevent too early saturation of the catching matrix. Determination of suitable affinities for the level of proteins secreted are determined empirically and are within the skill of one in the art.

Cells carrying large amounts of N-acetylneuraminic acid on their surface as a constituent of their lipopolysaccharides bear a negative charge at physiological pH values. Coupling of capture moieties can be via charge interactions. For example, moieties bearing polycations bind to negatively charged cells. Polycations are known in the art and include, for example, polylysine and chitosan. Chitosan is a polymer consisting of D-glucosamine groups linked together by α-(1-4) glucoside bonds.

Another method of coupling binding partners (which can comprise one or more capture moieties) to the cells is via coupling to the cell surface polysaccharides. Substances which bind to polysaccharides are known in the art, and include, for example, lectins, including concanavalin A, solanum tuberosum, aleuria aurantia, datura stramoniun, galanthus nivalis, helix pomatia, lens culinaris and other known lectins supplied by, a number of companies, including for example, Sigma Chemical Company and Aldrich Chemical Company.

In some embodiments of the invention, the product binding partner is coupled to the cell by hydrophobic anchoring to the cell membrane. Suitable hydrophobic groups that will interact with the lipid bilayer of the membrane are known in the art, and include, but are not limited to, fatty acids and non-ionic detergents (including, e.g., Tween-80). A drawback to attachment of the capture moiety to the cell via the insertion of a hydrophobic anchor is that the rate of integration of the hydrophobic moiety into the cell is low. Thus, high concentrations of the moiety with the hydrophobic anchor often are required. This latter situation is often uneconomical when the capture moiety is a relatively limited or expensive substance, for example, an antibody.

The low yield of hydrophobic molecules that embed themselves in the membrane is relevant only when these molecules are available in relatively limited quantities. This problem can be overcome by using a bridging system that includes an anchoring partner and a partner that contains the capture moiety, wherein one of the partners is of higher availability, and wherein the two parts of the bridging system have a high degree of specificity and affinity for each other. For example, in one embodiment avidin or streptavidin is attached to the cell surface via a hydrophobic anchor, while the partner with the product capture moiety are biotinylated anti-product antibodies. In another embodiment, the cell surface is labeled with digoxigenin followed by conjugates of anti-digoxigenin antibody fragments and anti-product antibodies. This approach can be used with other pairs of molecules able to form a link, including, for example, hapten with antihapten antibodies, NTA with polyhistidine residues, or lectins with polysaccharides. A preferred embodiment is one which allows "amplification" of the system by increasing the number of capture moieties per anchor moiety.

In one illustrative embodiment, a branched dextran is bound to palmitic acid, thus providing a multiplicity of available binding sites. The dextran is in turn coupled to biotin and treated with avidin-conjugated antibody specific for the product.

It is of course contemplated within the embodiments of the invention that bridging systems can be used between the anchor moiety and the capture moiety when the anchor moiety is coupled in any fashion to the cell surface. Thus, an avidin (or streptavidin) biotin linker moiety can link an antibody anchor moiety with a capture moiety. Bispecific antibody systems can also act as linker moieties.

In order to analyze and, if desired, to select cells that have the capability of secreting the product, cells modified as above to contain the capture moiety are incubated under conditions that allow the production and secretion of the product in a sufficient amount to allow binding to and detection of the cells that contain the captured product. These conditions are known to those of skill in the art and include, inter alia, appropriate temperature, pH, and concentrations of salts, growth factors and substrates in the incubation medium, as well as the appropriate concentrations of gas in the gaseous phase. When it is desirable to distinguish between high and low producer cells, the time of incubation is such that product secretion by the cells is still in a linear phase. The appropriate conditions can be determined empirically and such a determination is within the skill of one in the art.

Additionally, cell secretion can be modified, that is, upregulated, induced, or reduced using a biological modifier. The biological modifiers can be added at any time but are preferably added to the incubation medium. Alternatively, the cells can be pretreated with these agents or cells prior to the incubation step. Suitable biological modifiers include, but are not limited to, molecules and other cells. Suitable molecules include, but are not limited to, drugs, cytokines, small molecules, hormones, combinations of interleukins, lectins and other stimulating agents, e.g., PMA, LPS, bispecific antibodies and other agents that modify cellular functions or protein expression.

Suitable cells include, but are not limited to, direct cell to cell interactions such as between a tumor and T cell and indirect cell to cell interactions such as those induced by the proximity of other cells which secrete a biological modifier. Suitable cells include, but are not limited to, blood cells, peripheral bone marrow cells and various cell lines.

The incubation conditions are also such that product is essentially not captured or is captured to a much lesser extent by another cell, so as to distinguish non-producing cells from product producing cells, or high producers from low producers. Generally the incubation time is between five minutes and ten hours, and is more usually between one and five hours. The incubation medium can optionally include a substance that slows diffusion of the product from the producer cell. Substances which inhibit product diffusion in liquid media and that are non-toxic to cells are known in the art and include a variety of substances that partially or completely gel, including, for example, alginate, low melting agarose and gelatin. By varying the viscosity or permeability of the medium, the local captutre by a producing cell of differently sized products can be modulated. The molecular weight. size exclusion of the medium can be adjusted to optimize the reaction. The optimal composition of the medium can be empirically determined and is influenced by the cell concentration, the level of secretion and molecular weight of the product and the affinity of the capture moieties for the product. Such determinations are within the skill of one in the art.

Preferably, the gels are solubilized after the incubation to allow the isolation of the cells or groups of cells from the media by cell sorting techniques. Thus, for example, the gels can be linked by disulfide bonds that can be dissociated by sulfhydryl reducing agents such as β-mercaptoethanol or dithiothreitol, or the gels can contain ion cross-linkings, including for example, calcium ions, that are solubilized by the addition of a chelating agent such as EDTA.

At the end of the secretion phase the cells are usually chilled to prevent further secretion, and the gel matrix (if any) is solubilized. This order can, of course, be reversed. As capping can take place after the capture moiety is added due to cross linking, an incubation step to decrease capping can be added at this point. The cells can be incubated for instance in cytochalasin A or B or any other suitable substance that prevents capping. The cells containing the trapped product are then labeled with a label moiety. Labeling can be accomplished by any method known to those of skill in the art. For example, anti-product antibodies can be used to directly or indirectly label the cells containing the product. The labels used are those which are suitable for use in systems in which cells are to be analyzed or sorted based upon the attachment of the label moiety to the product.

In other embodiments, capture moieties that do not contain captured product can be detected. This allows, for example, the isolation of cells that secrete high amounts by employing a negative separation method, i.e., detection of cells not highly saturated with product. The cells can be labeled with other labeling substances recognizing, e.g., cell surface markers, cell type, cellular parameters such as DNA content, cell status, or number of capture moieties.

The enumeration of actual capture moieties can be important to compensate for varying amounts of these molecules due to, for example, different conjugation potentials of the cells. It can be especially important for the isolation of rare cells to exclude cells with decreased or increased capability for binding the product capture system, including the anchor and capture moieties. Alternatively, the reactions can proceed simultaneously in a "one-step reaction."

Cell Analysis and Cell Sorting

Analysis of the cell population and cell sorting based upon the presence of the label can be accomplished by a number of techniques known in the art. Cells can be analyzed or sorted by, for example, flow cytometry or FACS. These techniques allow the analysis and sorting according to one or more parameters of the cells. Usually one or multiple secretion parameters can be analyzed simultaneously in combination with other measurable parameters of the cell, including, but not limited to, cell type, cell surface markers, DNA content, etc. The data can be analyzed and cells sorted using any formula or combination of the measured parameters. Cell sorting and cell analysis methods are known in the art and are described in, for example, *The Handbook of Experimental Immunology*, Volumes 1 to 4, (D. N. Weir, editor); *Flow Cytometry Cell Sorting* (A. Radbruch, editor, Springer Verlag, 1992); and *Cell Separation Methods and Applications* (D. Recktenwald and A. Radbruch, eds., 1997) Marcel Dekker, Inc. N.Y. Cells can also be analyzed using microscopy techniques including, for example, laser scanning microscopy, fluorescence microscopy; techniques such as these can also be used in combination with image analysis systems. Other methods for cell sorting include, for example, panning and separation using affinity techniques, including those techniques using solid supports such as plates, beads and columns.

Some methods for cell sorting utilize magnetic separations, and some of these methods utilize magnetic beads. Different magnetic beads are available from a number of sources, including for example, Dynal (Norway), Advanced Magnetics (Cambridge, Mass., U.S.A.), Immuncon (Philadelphia, U.S.A.), Immunotec (Marseilles, France), and Miltenyi Biotec GmbH (Germany).

Preferred magnetic labeling methods include colloidal superparamagnetic particles in a size range of 5 to 200 nm, preferably in a size of 10 to 100 nm. These magnetic particles allow a quantitative magnetic labeling of cells, thus the amount of coupled magnetic label is proportional to the amount of bound product, and the magnetic separation methods are sensitive to different amounts of product secretion. Colloidal particles with various specificities are known in the art, and are available, for example, through Miltenyi Biotec GmbH. The use of immunospecific fluorescent or magnetic liposomes can also be used for quantitative labeling of captured product. In these cases, the liposomes contain magnetic material and/or fluorescent dyes conjugated with antibody on their surfaces, and magnetic separation is used to allow optimal separation between nonproducing, low producing, and high producing cells.

The magnetic separation can be accomplished with high efficiency by combining a second force to the attractive magnetic force, causing a separation based upon the different strengths of the two opposed forces. Typical opposed forces are, for example, forces induced by magnetic fluids mixed in the separation medium in the magnetic separation chamber, gravity, and viscous forces induced by flow speed of medium relative to the cell. Any magnetic separation method, preferably magnetic separation methods allowing quantitative separation will be used. It is also contemplated that different separation methods can be combined, for example, magnetic cell sorting can be combined with FACS, to increase the separation quality or to allow sorting by multiple parameters.

Preferred techniques include high gradient magnetic separation (HGMS), a procedure for selectively retaining magnetic materials in a chamber or column disposed in a magnetic field. In one application of this technique the product is labeled by attaching it to a magnetic particle. The attachment is generally through association of the product with a label moiety which is conjugated to a coating on the magnetic particle which provides a functional group for the conjugation. The captured product thus coupled to a magnetic "label", is suspended in a fluid which is then applied to the chamber. In the presence of a magnetic gradient supplied across the chamber, the magnetically labeled target cell is retained in the chamber; if the chamber contains a matrix, it becomes associated with the matrix. Cells which do not have or have only a low amount of magnetic labels pass through the chamber.

The retained cells can then be eluted by changing the strength of, or by eliminating, the magnetic field or by introducing a magnetic fluid. The selectivity for a captured product is supplied by the label moiety conjugated either directly or indirectly to the magnetic particle or by using a primary antibody and a magnetic particle recognizing the primary antibody. The chamber across which the magnetic field is applied is often provided with a matrix of a material of suitable magnetic susceptibility to induce a high magnetic field gradient locally in the camber in volumes close to the surface of the matrix. This permits the retention of fairly weakly magnetized particles. Publications describing a variety of HGMS systems are known in the art, and include, for example, U.S. Pat. Nos. 4,452,773, 4,230,685, PCT application WO85/04330, U.S. Pat. No. 4,770,183, and PCT/EP89/01602; systems are also described in U.S. Pat. Nos.

5,411,863; 5,543,289; 5,385,707; and 5,693,539, which are commonly owned and hereby incorporated herein by reference.

In addition, in other embodiments the processes include labeling the cells that contain the product captured by the capture moiety, if any. Other embodiments can also include analyzing the cell population to detect labeled cells, if any, and if desired, sorting the labeled cells, if any.

Diagnostic Methods for Detecting Antigen-specific T Cells

The present invention further provides diagnostic methods for detecting antigen-specific T cells. These include methods for analyzing a population of cells enriched for T cells to identify or enumerate antigen-specific T cells, as well as methods of determining a distribution of antigen-specific T cells that secrete a product in response to antigen stimulation.

Methods for analyzing a population of cells enriched in T cells to identify or enumerate antigen-specific T cells that secrete and release an amount of product relative to other cells in the population, wherein the product is secreted and released in response to antigen stimulation, comprise the steps of labeling the cells by the methods of the present invention; labeling the cells with at least one additional label that does not label the captured product; and detecting the amount of product label relative to the additional label. Such methods are useful, for example, in determining the proportion of a cell population that is specific for a given antigen. The method can be used to provide information regarding the immune status of an individual, including assessing an immune response to allergens, a tumor or virus, or evaluating the proportion of cells in an individual that are self reactive so as to detect or monitor autoimmune diseases.

Method of Treatment Using Enriched Antigen-specific T Cells

The present invention provides methods of treatment of a disease or condition related to a population of antigen-specific T cells, using the enriched T cells of the invention.

Treatment methods include those in which an antigen-specific T cell population is identified, enriched, and introduced into an individual; those in which a population of antigen-specific T cells is identified, enriched and expanded in vitro before introduction into an individual; those in which a population of antigen-specific T cells is identified and eliminated from a population of cells to be introduced into an individual; ex vivo genetic modification prior to administration; and selection of antigen-specific T cells selected according to cytokine expression. Examples of antigen-specific T cells selected according to cytokine expression include, but are not limited to, IFN-γ or TNF-α secreting CD8$^+$ T cells (cytotoxic) for treatment of cancer, viral (e.g. CMV, EBV) and bacterial (e.g. listeria, mycobacteria) infections; IFN-γ secreting CD4$^+$ T cells for the same indications and also for suppression and/or counter-regulation of allergy or vaccination against allergy, suppression of TH2-associated autoimmune diseases or vaccination against these autoimmune diseases; IL-10 or TGF-beta secreting CD4$^+$ T cells, for suppression TH1, but also TH2-associated autoimmune diseases or vaccination against these autoimmune diseases (tolerance induction); IL-4 secreting CD4$^+$ T cells for suppression of TH1-associated autoimmune diseases or vaccination against these autoimmune diseases; and IL-4 or IL-5 secreting CD4$^+$ T cells for treatment of helminth infections.

T cell populations enriched according to the methods of the present invention can be used to treat a variety of disorders. Included among these are cancer. T cells specific for a tumor antigen can be obtained using the methods of the present invention. Tumor cells can be obtained from an individual, and these can be co-cultured in vitro with T cells obtained from the same individual. After co-culturing the cells for a suitable time, tumor-specific T cells can be enriched according the methods of the present invention. This enriched population can then be re-introduced into the patient. Methods for anti-tumor immunotherapy using autologous T cells are known in the art. See, for example, WO 97/05239.

Alternatively, cells used in anti-tumor immunotherapy treatments can be allogeneic. Various modes of treatment of cancer with allogeneic T cells have been described in the art and can be used in the methods of the present invention. See, for example, PCT Publication No. WO 96/37208. Optionally, allogeneic T cells can be activated prior to introduction into an individual. Activation can be effected through contact with a biological modifier, an antibody directed to a cell surface marker, or a ligand or analog thereof for a cell surface receptor.

Another use of enriched T cell populations of the present invention is in immunomodulation, for example, in the treatment of autoimmune disorders, inflammatory disorders, allergies and hypersensitivities such as delayed-type hypersensitivity and contact hypersensitivity. T cells which are capable of destroying or suppressing the activity of autoreactive cells can be enriched in vitro, optionally expanded in vitro, then re-introduced into a patient. In the treatment of allergic responses, the ratio of TH1 to TH2 cells can be altered, or, cells reactive toward allergen-specific cells can be enriched and introduced into an individual.

Inducing T cell anergy can also be used to treat, ameliorate or prevent allograft rejection thus improving the results of organ transplantation and increasing the range of histotypes to which a patient can be made histocompatible.

Compositions comprising enriched T cell populations can further be used as vaccines, to prevent or substantially reduce the probability of the occurrence of a disease state such as a viral infection, autoimmune disorder, allergic response, cancer, or other disorder, or will reduce the severity or duration of the disease if subsequently infected or afflicted with the disease.

The compositions of cells can be administered by any known route, including, but not limited to, intravenously, parenterally, or locally. In the treatment methods of the present invention, enriched T cells are administered to an individual. The total number of cells, the number of doses, and the number of cells per dose will depend upon the condition being treated. Generally, about $10^6$ to $10^{11}$ cells are administered in a volume ranging from about 5 ml to 1 liter. The cells can be administered in a single dose or in several doses over selected time intervals. Of the cells being administered, preferably at least about 10%, more preferably at least about 20%, more preferably at least about 50%, are antigen-specific T cells which secrete a product.

Kits

It is contemplated that the reagents used in the detection of secretor cells of desired products can be packaged in the form of kits for convenience. The kits would contain, for example, optionally one or more materials for use in preparing gelatinous cell culture medium, the medium to be used for cell incubation for the production of the desired secreted product; a product capture system comprised of anchor and capture moieties; a label moiety; and instructions for use of the reagents. All the reagents would be packaged in appropriate containers.

The kit can also be formulated to include the following. In this case all the reagents are preferably placed in a single vial to which the cells are added. At least one antibody which is bispecific for a particular cell surface structure or anchor moiety and the product. At least one label moiety and, optionally, biological modifiers.

Optionally, the kit can include physiologically acceptable buffer. Such buffers are known in the art and include, but are not limited to, PBS with and without BSA, isotonic saline, cell culture media and any special medium required by the particular cell type. Buffers can be used that reduce cross-labeling and increase the local product concentration around the cells. Buffers can include agents for increasing viscosity or decreasing permeability. Suitable agents are described herein. The viscosity of the medium can be reduced before analysis by any method known in the art including, but not limited to, dissolution in a physiologically acceptable buffer, dissolving heat, EDTA, and enzymes. In the absence of added medium, cells already suspended in a medium can be directly added to the vial. Suitable cell suspensions include but are not limited to cell lines and biological samples. Biological samples include, but are not limited to, blood, urine and plasma.

Additional structures can be added for catching unbound product to reduce cell cross-contamination thereby reducing the diffusion of products away from the producing cells. These include, but are not limited to, anti-product antibody immobilized to gel elements, beads, magnetic beads, and polymers.

Biological modifiers can also be added to the buffer or medium to induce specific secretion.

Additional label moieties such as antibodies (magnetically or fluorescently labeled) can also be present, including, but not limited to anti-cell surface marker antibodies to identify cell types, propidium iodide to label dead cells, and magnetic beads to label certain cell types.

In this embodiment, all materials can be placed in a single container such as a vial and the cell sample added. The contents are incubated to allow secretion of a product and subsequent capture of the product and binding of the label moiety to the product. The cells which have secreted and bound product can then be separated and/or analyzed based on the presence, absence or amount of the captured product. Separation can be done by any of the methods known in the art, including, but not limited to, simple dilution, erythrocyte lysis, centrifugation-washing step, magnetic separation, FACS and Ficoll separation. The analysis of the cells can be performed by a variety of methods, including, but not limited to, FACS, image analysis, cytological labeling, and immunoassay.

The following examples are provided solely for the purposes of illustration and not to limit the scope of the invention. In light of the present disclosure, numerous embodiments within the scope of the claims will be apparent to those of ordinary skill in the art.

EXAMPLE 1

Peripheral blood mononuclear cells (PBMC) were cultured in complete RPMI 1640 (Gibco BRL, Grand Island, N.Y.) containing 100 U/ml penicillin, 0.1 mg/ml streptomycin, 0.3 mg/ml glutamine, 10 mM 2-mercaptoethanol and 10% human serum type AB (Sigma, St. Louis, Mo.) at a cell concentration of $2 \times 10^6$ cells/ml. Peptide M1 58–66 from Influenza virus matrix protein (GILGFVFTL; Neosystem, Strasbourg, France) was added to a final concentration of 1 $\mu$M. Control cells were cultured without peptide.

Cells were incubated at 37° C. in an atmosphere containing 7.5% $CO_2$. After 5 hours and 30 minutes, cells were harvested by centrifugation. Cells were incubated at a cell concentration of $5 \times 10^7$ cells/ml in complete RPMI 1640 with anti human interferon gamma (IFN-$\gamma$) monoclonal antibody (mAb) 4SB3 conjugated to anti-human CD45 mAb 5B1 (30 $\mu$g/ml) at 8° C. for 7 min. The cells were then diluted to $2 \times 10^6$ cells/ml with complete RPMI 1640 containing 10% FCS and incubated for 45 minutes at 37° C. Then cells were pelleted and incubated with phycoerythrin (PE)-conjugated anti human interferon gamma (IFN-$\gamma$) mAb NIB42 (4 $\mu$g/ml) and FITC-labeled anti-CD8 mAb in PBS/BSA/EDTA solution 0.05% BSA and 2 mM EDTA, for 10 minutes at 4° C. Cells were then washed in PBS/BSA/EDTA and labeled with mouse anti-PE mAb 80-5 conjugated to MicroBeads (Miltenyi Biotec) in PBS/BSA/EDTA for 15 minutes at 8° C. Cells were washed and resuspended in 500 $\mu$l PBS/BSA/EDTA.

IFN-$\gamma$-secreting cells were enriched with the magnetic cell separation system MACS. Magnetically labeled cell suspension was pipetted onto a MiniMACS separation column in a MiniMACS separation unit, the cell suspension was allowed to pass through and the column was washed with $3 \times 500$ $\mu$l buffer. The effluent was collected as negative fraction (N1). The column was removed from the separator, and placed on a suitable tube. 1 ml buffer was pipetted on top of column and magnetically labeled cells were flushed out using a plunger and applied to a second round of MiniMACS separation.

The original cells (i.e., before MACS separation), negative cell fractions (of first as well as second MACS separation, designated N1 and N2, respectively) and positive cell fraction (P2) of second MACS separation were analyzed by flow cytometry. FACScan and CELLQuest research software (Becton Dickinson, Mountain View, Calif.) were used for flow cytometric analysis. Dead cells and cell debris were excluded according to scatter properties and staining with propidium iodide (PI; 0.3 $\mu$g/ml).

Figure 1H:
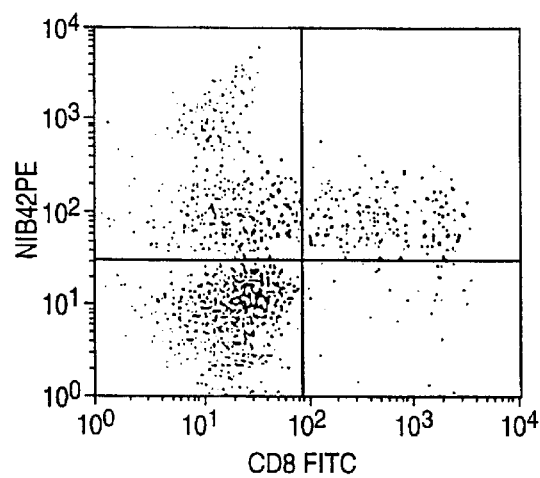
Figure 1I:
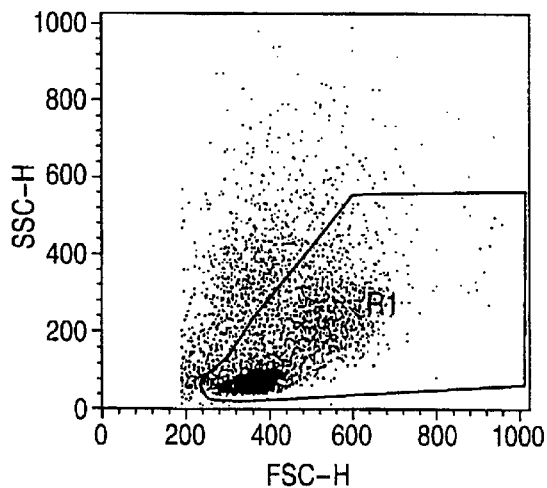
Figure 1J:
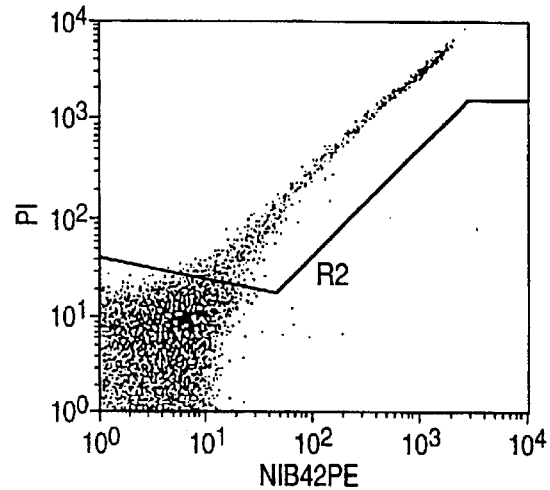
Figure 1K:
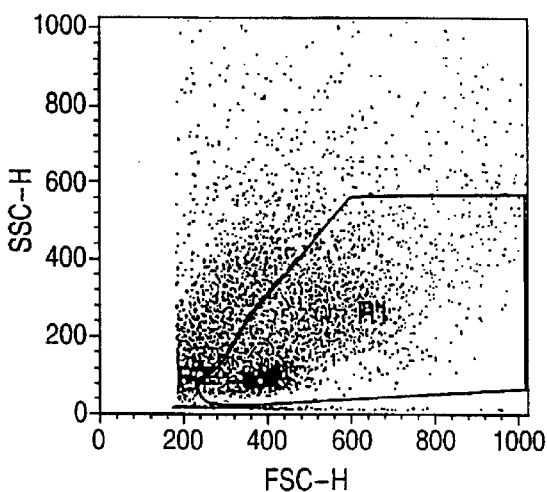
Figure 1L:
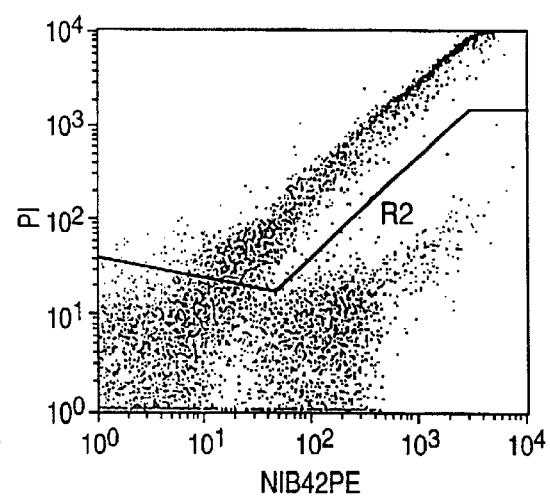
Figure 1M:
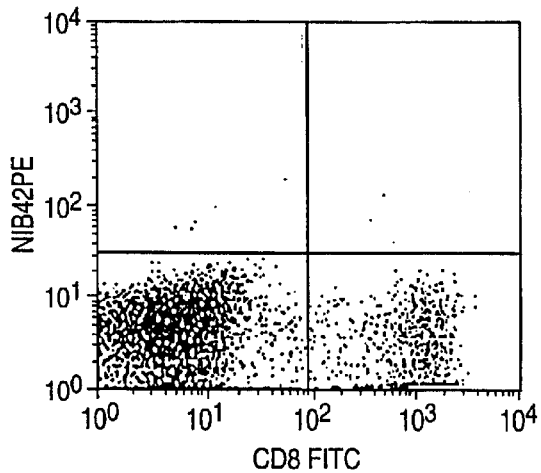
Figure 1N:
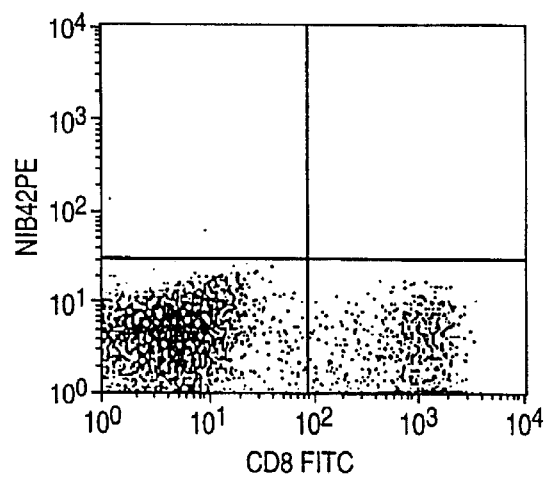
Figure 1O:
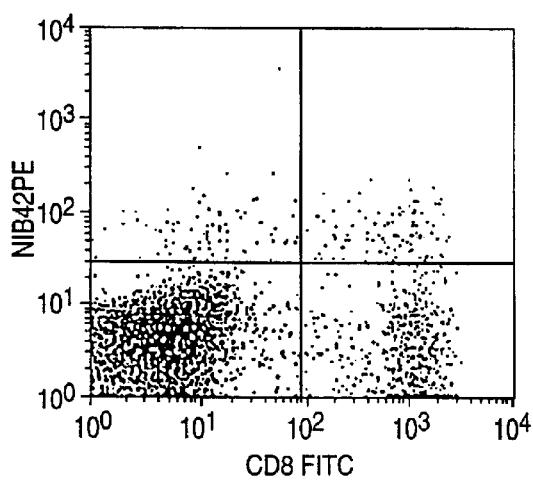
Figure 1P:
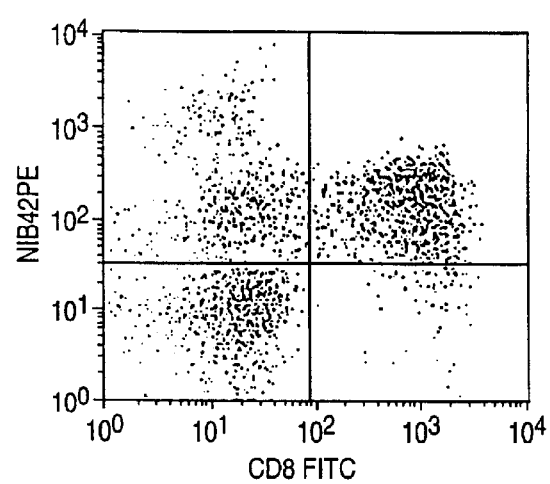
Figure 2A:
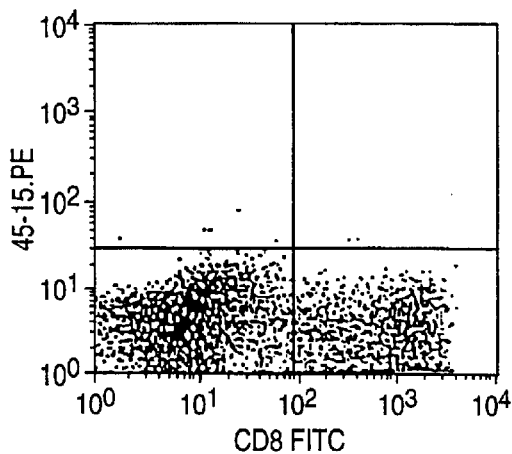
FIGS. 2A–N are FACS plots showing analysis of cells subjected to the separation protocol described in Example 2. A–G show analysis of control cells cultured with no peptide; N–R show analysis of peptide-stimulated cells. A–D and H–K show FITC-labeled anti-CD8 versus PE-labeled anti-IFN-γ staining of the starting cell population (A and J), the first negative population (B and I), the second negative population (C and J) and the enriched cell population (D and K). F and M show staining for Vβ17TCR of the enriched cell population.
Figure 2B:
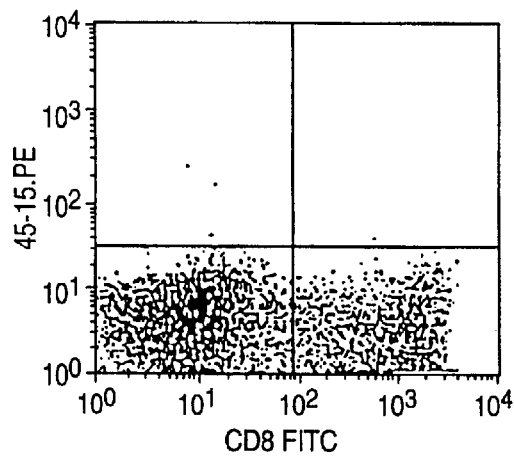
Figure 2C:
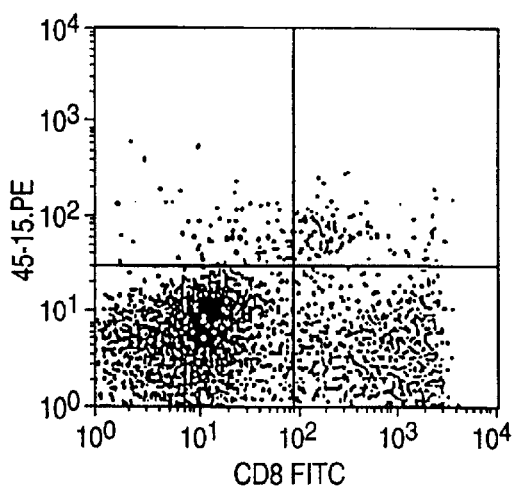
Figure 2D:
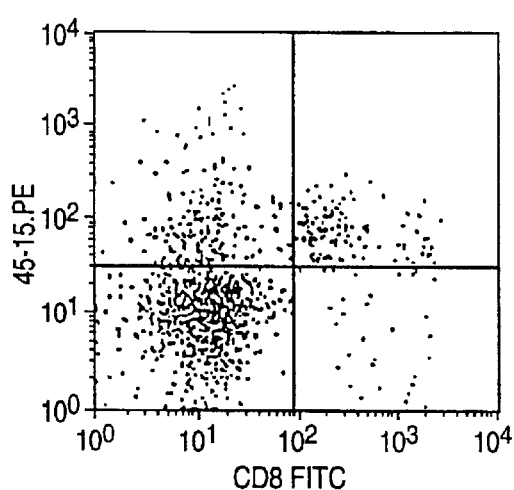
Figure 2E:
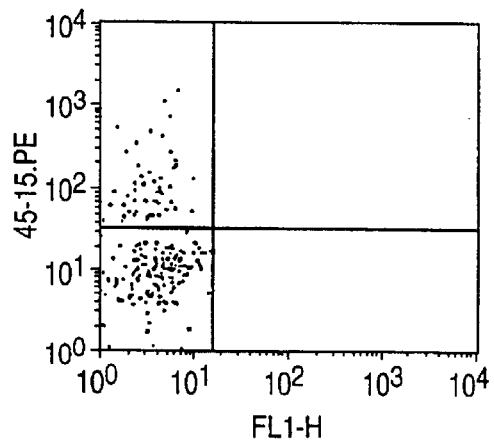
Figure 2F:
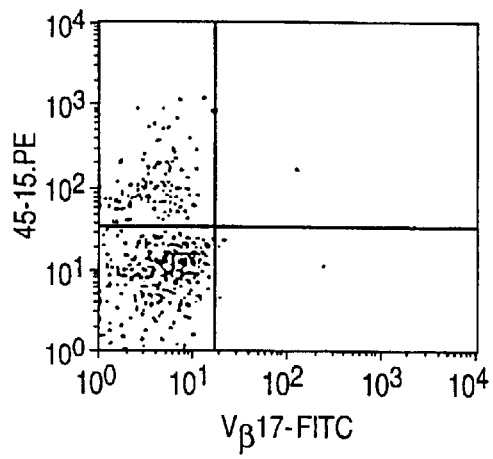
Figure 2G:
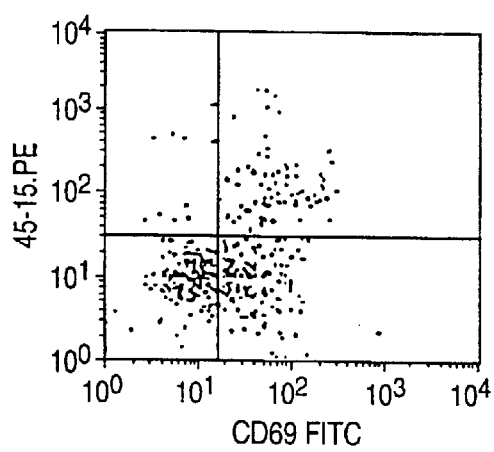
Figure 2H:
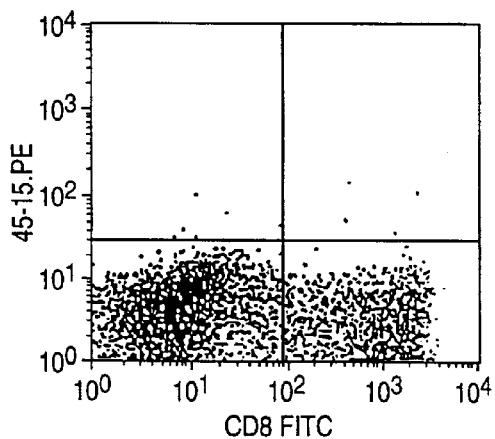
Figure 2I:
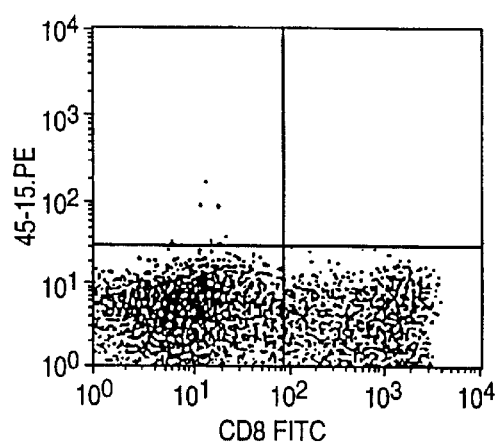
Figure 2J:
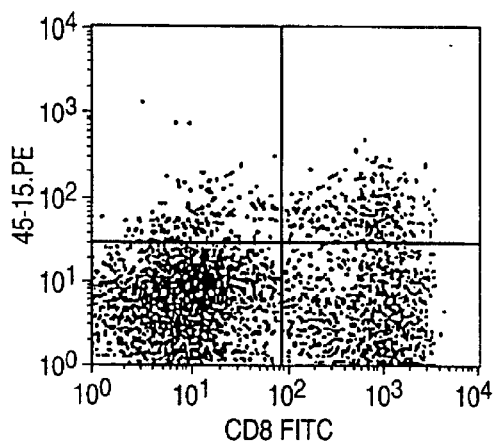
Figure 2K:
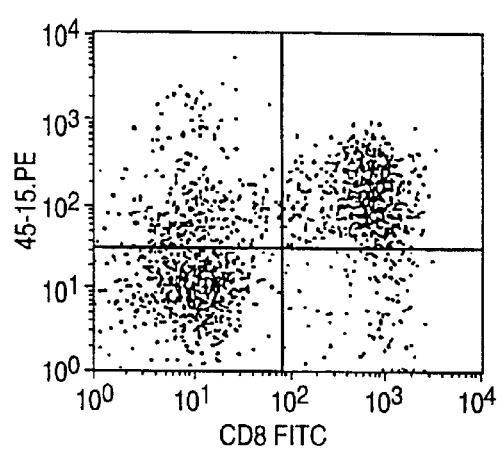
Figure 2L:
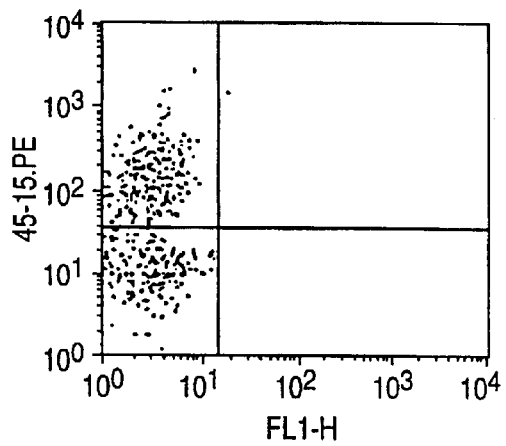
Figure 2M:
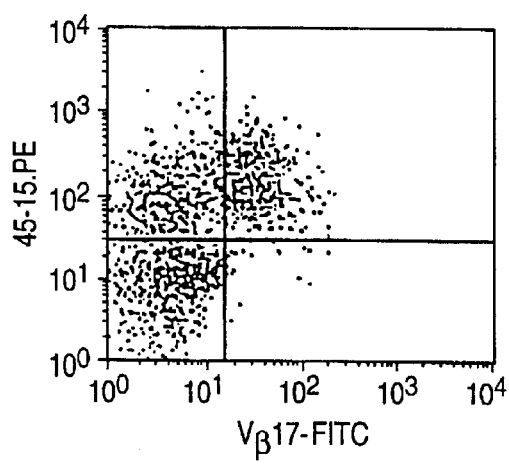
Figure 2N:
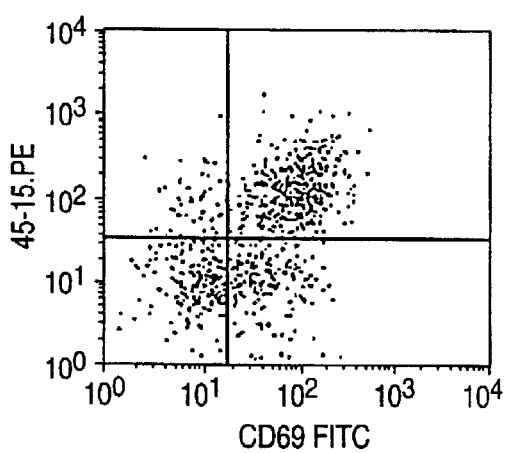

The results are shown in FIGS. 1A–P. While dot plots A–H show analysis of control cells cultured without peptide, plots I–P show analysis of peptide stimulated cells. Dot plots show the scatter properties of the starting cell population (A and I) and the enriched cell populations (C and K); and PI versus PE fluorescence of the starting cell population (B and J) and enriched cell population (D and L).

Dot plots E–H and M–P show anti-CD8-FITC versus anti-IFN-$\gamma$-PE staining of gated cells in original (E and M), first negative (F and N), second negative (G and O) and in the final positive cell fraction (H and P).

The control cell population, $CD8^+$ IFN-$\gamma^+$ cells were enriched up to 11% among live cells (FIG. 1H), in the peptide stimulated cell population, $CD8^+$ IFN-$\gamma^+$ cells were enriched up to 40% (FIG. 1P). From a starting population of $3.5 \times 10^7$ control cells, about 600 $CD8^+$ IFN-$\gamma^+$ cells were isolated, compared to 4100 CD8+ IFN-$\gamma^+$ cells isolated from a starting population of $3.5 \times 10^7$ peptide-stimulated cells.

CD8− cells brightly stained with PE-labeled anti-IFN-$\gamma$ were $CD19^+$ B cells, most likely B cells specific for a sorting reagent, probably PE. These cells were enriched to the same extent from control cells compared to peptide stimulated cells.

Also the $CD8^-$ cells dimly stained with PE-labeled anti-IFN-$\gamma$ (like the $CD8^+$ IFN-$\gamma^+$ cells) were enriched to the same extent from control cells compared to peptide stimulated cells. Such cells partially stain for CD4 and CD56, and therefore are most likely T helper cells or NK cells secreting IFN-$\gamma$.

Thus there is a basal level of IFN-$\gamma$ secretion by ($CD4^+$) T helper cells, ($CD8^+$) cytotoxic T cells and (CD56+) NK cells without intentional antigen-specific stimulation in vitro, which reflects most likely the IFN-γ secretion induced already in vivo in ongoing immune responses at the time of blood sampling.

However, IFN-γ+-secreting CD8+ cells induced by stimulation with the HLA class I-restricted influenza peptide M1 58–66 were significantly enriched above this background level; therefore, most of the CD8+ IFN-γ+ cells enriched from peptide stimulated cells are peptide-specific T cells. Specificity of enriched cells was further confirmed by staining for the presence of Vβ17 TCR, which is a conserved T cell receptor (TCR) segment in M1 58–66 specific cytotoxic T cells. Lehner et al. (1995) *J. Exp. Med* 181:79–91; and Lalvani et al. (1997) *J. Exp. Med.* 186:859–865. Among IFN-γ+ cells isolated from peptide stimulated cells, but not among IFN-γ+ cells isolated from control cells, most express Vβ17+ TCRs.

EXAMPLE 2

Peripheral blood mononuclear cells (PBMC) were cultured in complete RPMI 1640 (Gibco BRL, Grand Island, N.Y.) containing 100 U/ml penicillin, 0.1 mg/ml streptomycin, 0.3 mg/ml glutamine, 10 mM 2-ME and 10% human serum type AB (Sigma, St. Louis, Mo.) at $2 \times 10^6$ cells/ml. Peptide M1 58–66 from Influenza virus matrix protein (GILGFVFTL; Neosystem, Strasbourg, France) was added to a final concentration of 1 μM. Control cells were cultured without peptide.

After 5 hours and 30 minutes cells were harvested by centrifugation. Cells were incubated at $5 \times 10^7$ cells/ml in complete RPMI 1640 with anti-human IFN-γ mAb 4SB3 conjugated to anti-human CD45 mAb 5B1 (30 μg/ml) at 8° C. for 7 minutes. The cells were then diluted to $2 \times 10^6$ cells/ml with complete RPMI 1640 containing 10% FCS and incubated for 45 minutes at 37° C. Then cells were spun down and incubated with phycoerythrin (PE)-conjugated anti-human-IFN-γ mAb NIB42 (4 μg/ml) and FITC-labeled anti-CD8 in PBS/BSA/EDTA, for 10 minutes at 4° C. Cells were then washed in PBS/BSA/EDTA and labeled with mouse anti-PE mAb 80–5 conjugated MicroBeads (Miltenyi Biotec) in PBS/BSA/EDTA for 15 minutes at 8° C. Cells were washed and resuspended in 500 μl PBS/BSA/EDTA.

IFN-γ-secreting cells were enriched with the magnetic cell separation system MACS. Magnetically labeled cell suspension was pipetted on top of a MiniMACS separation column in a MiniMACS separation unit, cell suspension was allowed to pass through and column was washed with 3×500 μl buffer. Effluent was collected as negative fraction. The column was removed from separator, and placed on a suitable tube. 1 ml buffer was pipetted on top of column and magnetically labeled cells were flushed out using a plunger and applied to a second round of MiniMACS separation.

Original cells (i.e., before MACS separation), negative cell fractions (of first as well as second MACS separation) and positive cell fraction of second MACS separation were analyzed by flow cytometry. FACScan and CELLQuest research software (Becton Dickinson, Mountain View, Calif.) were used for flow cytometric analysis. Dead cells and cell debris were excluded according to scatter properties and staining with propidium iodide (PI; 0.3 μg/ml) as shown in Example 1. The results are shown in FIG. 2.

While dot plots 2A–G show analysis of control cells cultured without peptide, plots 2J–R show analysis of peptide stimulated cells.

Dot plots 2A–D and 2J–M show FITC-labeled anti-CD8 versus PE-labeled anti-IFN-γ staining of gated cells in original (A, J), first negative (B, K), second negative (C, L) and in the final positive cell fraction (D, M).

While in the control cells CD8+ IFN-γ+ cells were enriched up to 8.2% among live cells (2D), out of peptide stimulated cells CD8+ IFN-γ+ cells were enriched up to 41.6% (2M). Out of $6.1 \times 10^7$ control cells, about 1360 CD8+ IFN-γ+ cells were isolated compared to 11700 CD8+ IFN-γ+ cells out of $6.9 \times 10^7$ peptide stimulated cells.

IFN-γ+ secreting CD8+ cells induced by stimulation with the HLA class I-restricted influenza peptide M1 58–66 were significantly enriched above background level, i.e., most of the CD8+ IFN-γ+ cells enriched from peptide stimulated cells must be peptide-specific T cells. Specificity of enriched cells was further confirmed by staining against Vβ17 TCR, which is a conserved T cell receptor (TCR) segment in M1 58–66 specific cytotoxic T cells (Lehner 1995; Lalvani 1997). Only among IFN-γ+ cells isolated from peptide stimulated cells, but not among IFN-γ+ cells isolated from gcontrol cells, most express Vβ17+ TCRs (2F versus 2O).

The following examples show that appropriate antigen-specific stimulation, CD4+ and CD8+ lymphocytes rapidly express cytokines. The technique is demonstrated here for HLA-A0201-restricted influenza matrix protein (FLU) peptide 58–66-specific CD8+ cytotoxic T lymphocytes (CTLs), influenza A virus- and recombinant tetanus toxin C (rTT.C)-fragment-specific T helper type 1 (Th1) cells, and tetanus toxoid (TT) specific T helper type 2 (Th2) cells.

EXAMPLE 3

Materials and Methods for Examples 4–8
Cells and ex vivo Stimulation

Buffy coats were obtained from the Institute for Transfusions medicine, Hospital Merheim, Cologne, Germany and, if necessary, selected on the basis of HLA-type. PBMC were prepared by standard Ficoll-Pacque (Pharmacia, Uppsala, Sweden) density gradient centrifugation, washed twice in PBS and resuspended at a cell concentration of $2 \times 10^6$ cells per ml in cell culture medium consisting of RPMI 1640 (Life Technologies, Paisley, UK) supplemented with 10% (wt/vol) human AB-serum (Boehringer Ingelheim, Ingelheim, Germany), 1 mM L-alanyl-glutamine (Life Technologies), 100 U/ml penicillin/streptomycin (Life Technologies), 0.05 mM 2-mercaptoethanol (Life Technologies) and 1 mM sodium-pyruvate (Life Technologies). 12.5 ml of the cell suspension were place in 100×20 mm tissue culture dishes (Sarstedt, Newton, Mass.) and FLU 58–66 peptide (Neosystems, Strasbourg, France) was added to a final concentration of 1 μM, purified influenza A virus preparation (Biodesign, Kennebunk, Me.) was added to a final concentration of μg/ml, rTT.C (Boehringer Mannheim, Mannheim, Germany) was added to a final concentration of 7 μg/ml and purified TT (Statens Serum Institut, Copenhagen, Denmark) was added to a final concentration of 1 μg/ml. Cells were incubated at 37° C. in a humidified 7.5% $CO_2$ atmosphere for 5–10 h.

Capturing of Secreted Cytokines by Cellular Affinity Matrices

Ab-Ab conjugates directed against CD45 and either IL-4 or IFN-γ were produced by standard protein coupling techniques. Aslam et al. (1998) Bioconjugation, Macmillan Reference Ltd., London. After the ex vivo stimulation, cells were harvested using a disposable cell scraper (Costar, Cambridge, Mass.) and labeled for 7 min at a cell concentration of $10^8$ cells per ml in ice-cold medium with 50 μg per ml of the Ab-Ab conjugates. Then, cells were diluted with medium to a final cell concentration of $2 \times 10^6$ cells per ml and allowed to secrete for 45 min at 37° C. in a humidified 7.5% $CO_2$ atmosphere.

Magnetic Enrichment and Detection of Cytokine Secreting Cells

After the cytokine capturing period, cells were harvested again, resuspended at a cell concentration of $10^8$ cells per ml in phosphate-buffered saline containing 0.5% (w/v) bovine serum albumin and 5 mM EDTA (buffer) and stained for 10 min at +4° C. with 5 μg/ml anti IFN-γ-PE or anti IL-4-PE, respectively. Cells were washed with buffer (300×g, 10 min), resuspended in 400 μl buffer and magnetically labeled for 15 min at +4° C. with 100 μl anti PE Ab-microbeads (Miltenyi Biotec, Bergisch, Gladbach, Germany). After washing, the cells were applied onto a MS+ column and placed in a MiniMACS magnet (Miltenyi Biotech). The column was rinsed with buffer and the retained cells were eluted from the column after removing it from the magnetic field to achieve a higher enrichment rate, the eluted cells from the first column were applied to another MS+ column and the magnetic separation was repeated. Cell samples were analyzed on a FACScalibur flow cytometer (Becton Dickinson, San Jose, Calif.) using the CellQuest software package.

Magnetic Enrichment and Detection of Cytokine Secreting Cells

For detection, enumeration and phenotyping of cytokine-secreting cells the following reagents were used: anti IFN-γ-CD45 (anti IFN-γ, clone 4SB3; CD45, clone 5B1, W. Knapp, Vienna, Austria), anti IFN-γ-PE (clone 45–15), anti IL-4-CD45 (anti IL-4, clone 1 A6-10; CD45, clone 5B1, W. Knapp Vienna, Austria), anti IL-4-PE (clone 7A3-3), CD8-Cy5 (clone BM135/80, Behring Diagnostics, Marburg, Germany), CD4-Cy5 (clone M-T321, Behring), CD4-FITC (clone SK3, Becton Dickinson), CD27-FITC (clone M-T271, Pharmingen, San Diego, Calif.), CD28-FITC (clone CD28.2, Pharmingen) CD57-FITC (clone HNK-1, Becton Dickinson), anti Vβ17.FITC (clone E17.5F3.15.13, Coulter-Immunotech, Marseille, France). Meager et al. (1984) *Interferon Res.* 4:619–625; Alkan et al. (1994) *J. Immunoassay* 15:217–225; and Bird et al. (1991) *Cytokine* 3:562–567.

Cytolytic Activity Assay

The cytotoxic activity of enriched cytokine-secreting cells was analyzed using a flow cytometry-based assay which has been described previously. Mattis et al. (1997) *J. Immunol. Met.* 204:135–142. Briefly, $1×10^6$ HLA-A2.1$^+$ T2 cells were labeled with 4 μg per ml of the green fluorescent dye DiO (Molecular Probes, Eugene, Oreg.) in phosphate-buffered saline containing 5 mM EDTA and 3% fetal calf serum for 45 min at 37° C. Cells were washed three times with buffer, resuspended in cell culture medium and loaded with 1 μM Flu 58–66 peptide or Melan A/MART 1 27–35 peptide (Bachem, Heidelberg, Germany) overnight at 37° C. in a humidified 7.5% $CO_2$ atmosphere. Enriched cytokine-secreting cells were expanded for 18 d in tissue culture in the presence of recombinant human IL-2 (Peprotech, London, U.K.). Expanded cytokine-secreting cells and peptide-loaded DiO-labeled HLA-A2.1$^+$ T2 cells were co-cultivated for 16 h at a ratio of 1:1 at 37° C. in a humidified 7.5% $CO_2$ atmosphere. After the culture period, cells were harvested and analyzed by flow cytometry. In order to permit discrimination between live and dead DiO-labeled T2 cells, samples were counterstained with the red fluorescent exclusion dye propidium iodide.

EXAMPLE 4

The capability to secrete effector cytokines like IFN-γ following short-term antigenic restimulation with synthetic peptide- or native antigen-pulsed APCs is a typical feature of memory/effector CD4$^+$ (Th1-type) and CD8$^+$ T cells. Salmon et al. (1989) *J. Immunol.* 143:907–912; and Hamaan et al. (1997) 186:1407–1418. To isolate low-frequency memory/effector antigen-specific CD4$^+$ and CD8$^+$ T cells directly from peripheral blood based on antigen-induced secretion of IFN-γ and cellular affinity matrix technology, peripheral blood mononuclear cells (PBMC) from HLA-matched adult healthy blood donors were stimulated for 5–6 h with: (a) the HLA-A0201-restricted FLU peptide 58–66, (b) a purified influenza A virus preparation and (c) rTT.C. After the stimulation period, an affinity matrix for IFN-γ was created on the cell surface using antibody (Ab)-Ab conjugates directed against CD45 and IFN-γ, and the cells were allowed to secrete IFN-γ in culture for 45 min. Then, IFN-γ, relocated to the affinity matrix of the secreting cells, was stained with a phycoerythrin (PE)-conjugated IFN-γ-specific Ab, and PE-labeled cells were enriched by MACS using anti PE Ab microbeads. See, also, Brosterhus et al., 10th Int. Congress in Immunology, New Delhi, India, Nov. 1–6, 1998, pp. 1469–1473.

Figure 3A:
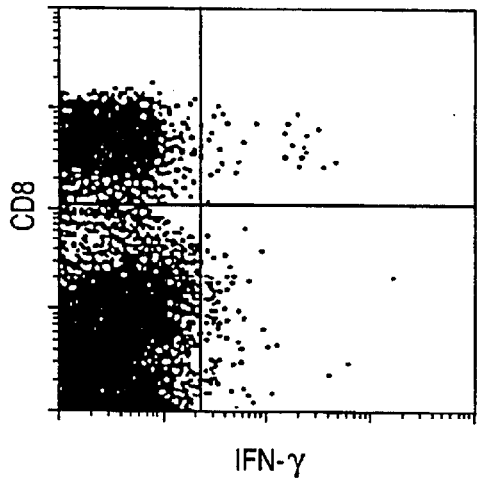
FIG. 3 is a series of dot plots showing IFN-γ-secretion-based enrichment and detection of live antigen-specific $CD4^+$ and $CD8^+$ T cells. Dot plots show CD8-Cy5 vs. anti IFN-γ-PE (A–D) or CD4-Cy5 vs. anti IFN-γ-PE (E–L) staining of PBMC from healthy adult donors stimulated with (A,B) or without (C,D) the HLA-A0201-restricted FLU 58–66 peptide, a purified influenza A virus preparation (with (E,F) without (G,H)) and rTT.C (with (I,J) without (K,L)) before (A,C,E,G,I,K) and after (B,D,F,H,J,L) magnetic enrichment of IFN-γ-secreting cells. Live lymphocytes were gated according to light-scatter properties and propidium iodide exclusion.
Figure 3B:
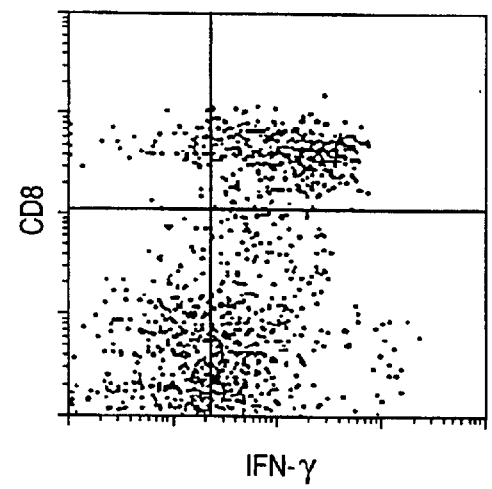
Figure 3C:
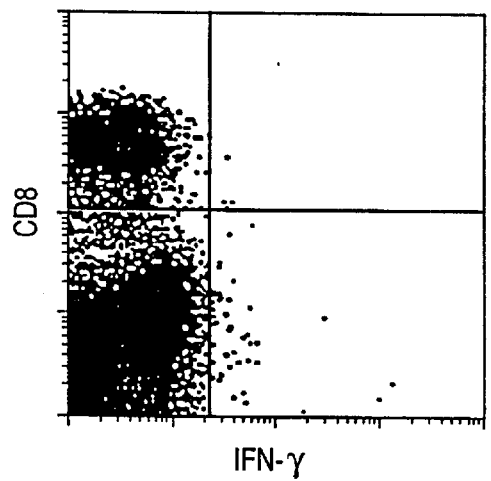
Figure 3D:
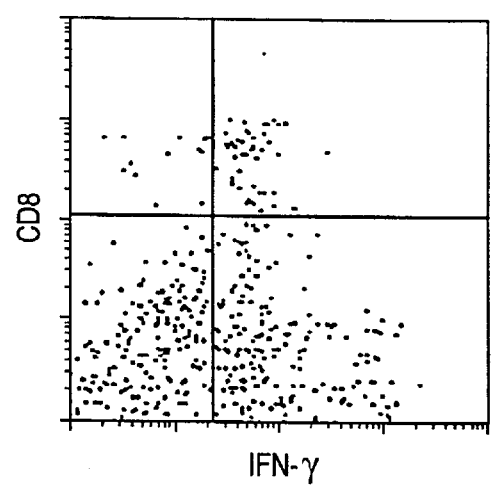
Figure 3E:
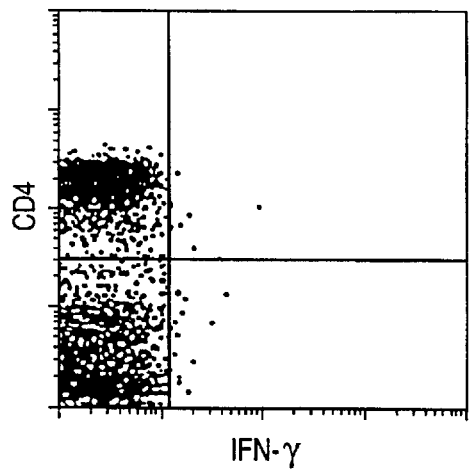
Figure 3F:
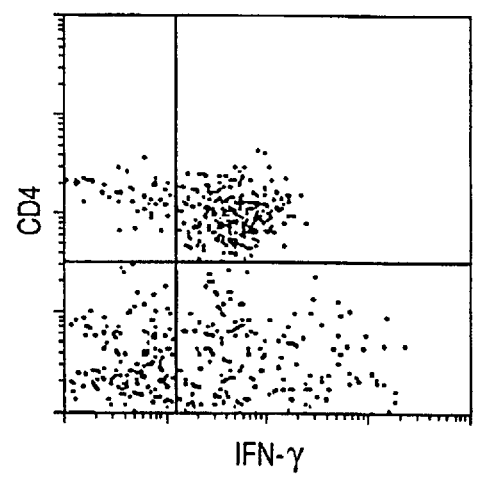
Figure 3G:
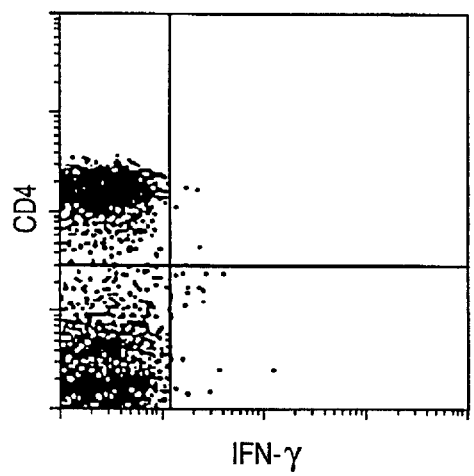
Figure 3H:
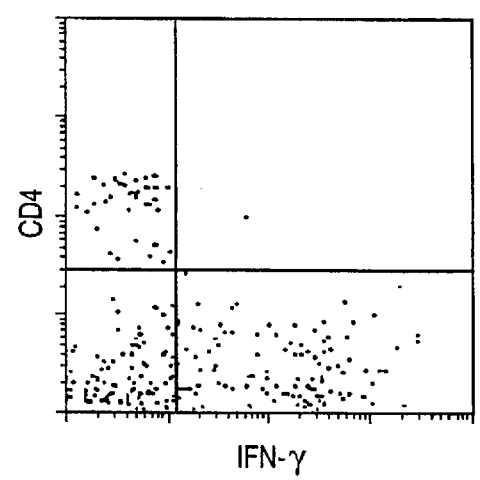
Figure 3I:
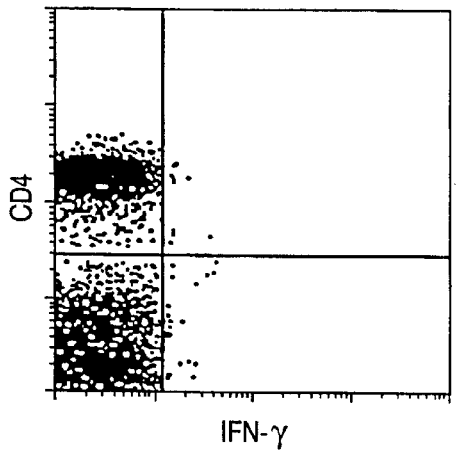
Figure 3J:
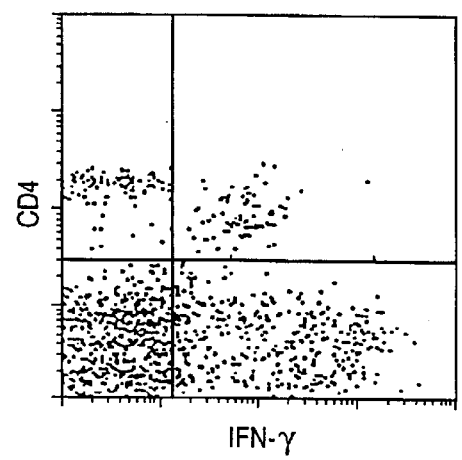
Figure 3K:
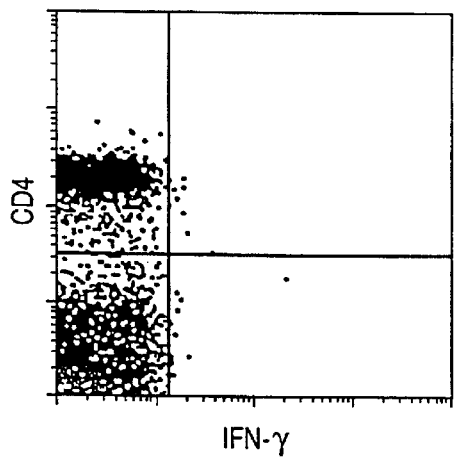
Figure 3L:
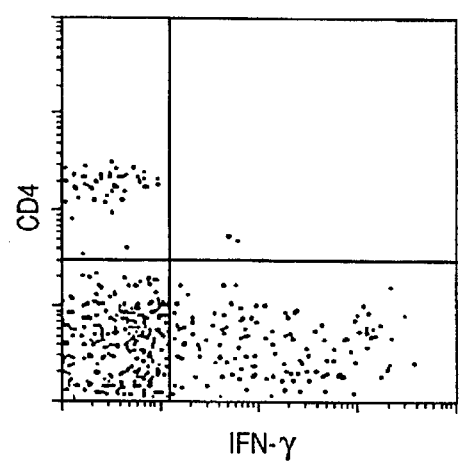
Figure 4A:
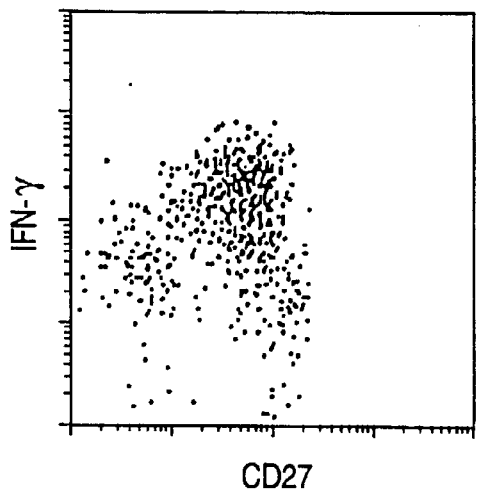
FIG. 4 is a series of dot plots showing a phenotypic analysis of enriched Flu 58–66 peptide-specific $CD8^+$ T cells. Enriched IFN-γ-secreting $CD8^+$ T cells from FLU 58–66 peptide-stimulated PBMC (A,B,E,F) and, for control, from non-stimulated PBMC (C,D,G,H) were stained with anti IFN-γ-PE and counterstained with FITC-conjugated antibodies against CD27, CD28, CD57 and the TCR Vβ17 chain. Light-scatter properties, propidium iodide and CD8-Cy5 staining were used for gating of live $CD8^+$ T cells.
Figure 4B:
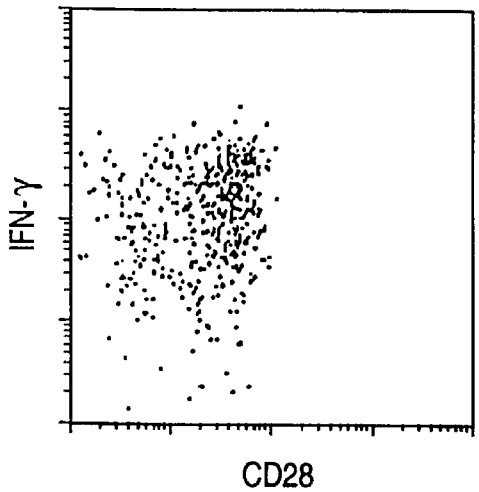
Figure 4C:
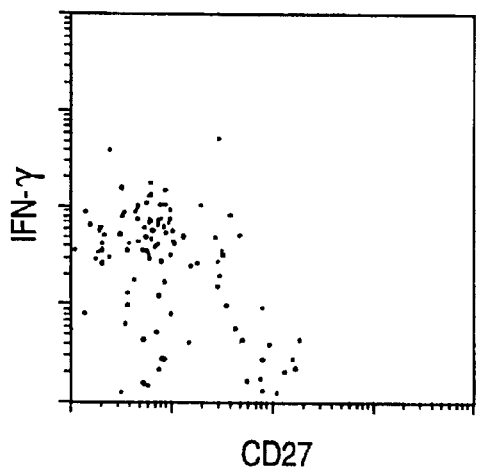
Figure 4D:
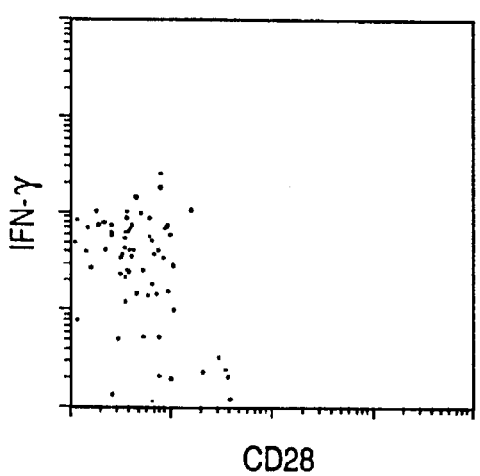
Figure 4E:
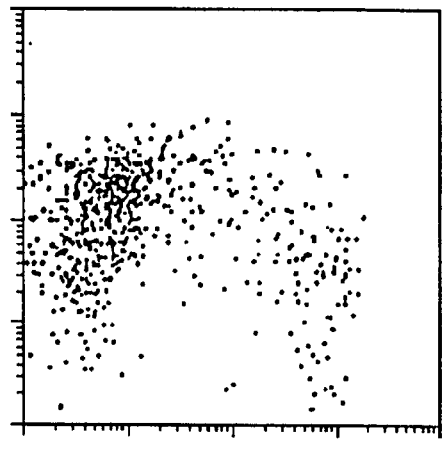
Figure 4F:
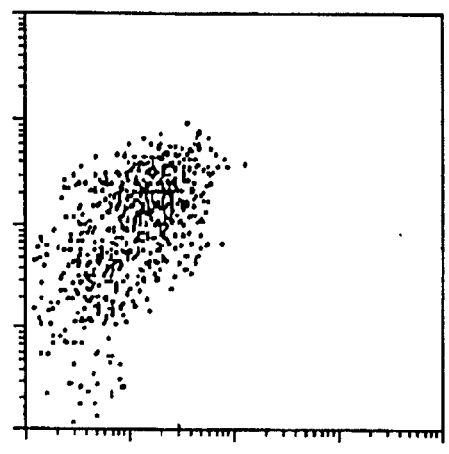
Figure 4G:
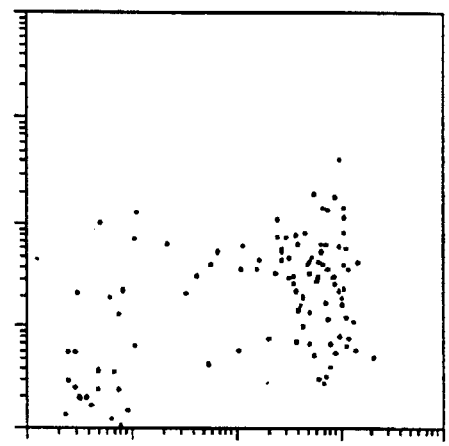
Figure 4H:
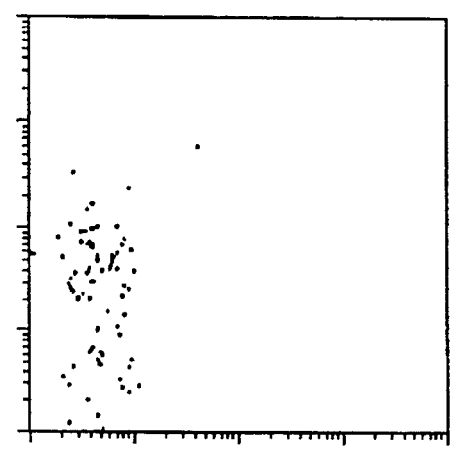

Compared with the non-stimulated control samples, a significantly higher proportion of IFN-γ-secreting CD8$^+$ cells were detectable after enrichment in the FLU 58–66 peptide-stimulated sample (FIG. 3A: 38.3% vs. 13.7%), and significantly higher proportions of IFN-γ-secreting CD4$^+$ cells were detectable after enrichment in the samples stimulated with the influenza A virus preparation (FIG. 3B: 35.5% vs. 1.1%) and rTT.C (FIG. 3C: 6.1% vs. 0.3%), respectively. When looking at the absolute numbers of enriched IFN-γ-secreting T cells and their frequencies among total PBMC, differences between the stimulated and non-stimulated samples are even more remarkable: (a) 12,500 IFN-γ-secreting CD8$^+$ T cells were isolated from $5.3×10^7$ FLU 58–66 peptide-stimulated PBMC (frequency 1 in 4,200) and 1370 IFN-γ-secreting CD8$^+$ T cells were isolated from $5.1×10^7$ non-stimulated PBMC (frequency: 1 in 37,000); (b) 351 IFN-γ-secreting CD4$^+$ T cells were isolated from $5×10^6$ influenza A virus-stimulated PBMC (frequency 1 in 14,000) and 4 IFN-γ-secreting CD4$^+$ T cells were isolated from $5.0×10^6$ non-stimulated PBMC (frequency 1 in 1,250,000); and (c) 132 IFN-γ-secreting CD4$^+$ T cells were isolated from $1.8×10^7$ rTT.C-stimulated PBMC (frequency: 1 in 136,000) and 7 IFN-γ-secreting CD4$^+$ T cells were isolated from $1.9×10^7$ non-stimulated PBMC (frequency: ~1 in 2,710,000). Considering these experimental results, it is evident that IFN-γ-secreting T cells present at frequencies of below $10^{-6}$ can be detected with our technique.

EXAMPLE 5

Both memory-and effector-type CD8$^+$ T cells are capable of secreting IFN-γ. Hamann et al. (1997). To determine the phenotype of FLU 58–66 peptide-specific CD8$^+$ T cells, enriched IFN-γ-secreting CD8$^+$ T cells from the FLU 58–66 peptide-stimulated sample and the control sample were analyzed by three-color immunofluorescence for the expression of a panel of leukocyte surface markers that allow to distinguish between memory and effector-type CD8$^+$ T cells. Hamann et al. As shown in FIG. 2, most FLU 58–66 peptide-specific CD8$^+$ T cells were (1997) CD27$^+$, CD28$^+$ and CD57$^-$, consistent with a memory phenotype, whereas most of the IFN-γ-secreting CD8$^+$ T which became isolated independent of the FLU 58–66 peptide were CD27$^-$, CD28$^-$, CD57$^+$, consistent with an effector phenotype. The latter could have been induced in vivo to secrete IFN-γ and thus might reflect ongoing immune responses.

More than 54.8% of the IFN-γ-secreting CD8$^+$ T cells from the FLU 58–66 peptide-stimulated sample expressed the Vβ17 TCR chain, compared with less than 2.2% of the IFN-γ-secreting CD8⁺ T cells from the control sample (FIG. 4). This confirms previous reports showing a bias of HLA-A0201-restricted FLU peptide 58–66-specific CD8⁺ T cells towards the use of VPβ17 TCR chain, first in cloned CTLs and later, using fluorescent tetramers of FLU 58–66 peptide-loaded HLA-A2.1 molecules, also in PBMC. Lehner et al. (1995) *J. Exp. Med.* 181:79–91; and Dunbar et al. (1998).

EXAMPLE 6

Figure 5:
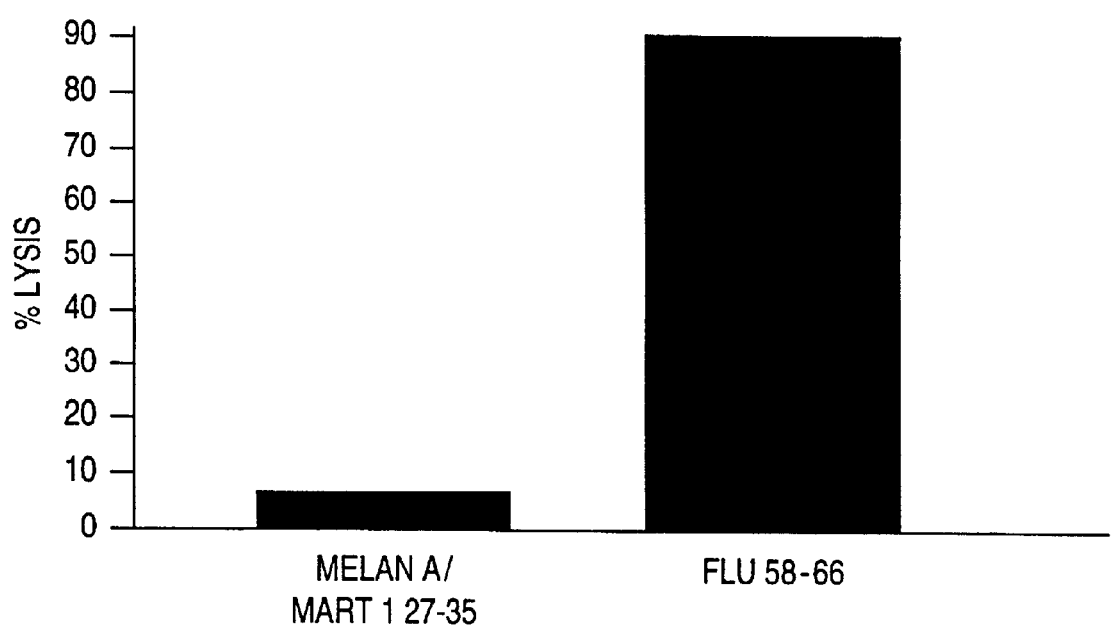
FIG. 5 is a graph depicting cytolytic activity of enriched and expanded Flu 58–66 peptide-specific T cells. IFN-γ-secreting $CD8^+$ T cells from FLU 58–66 peptide-stimulated PBMC were expanded for 18 days in tissue culture in the presence of IL-2 and then assayed for CTL activity assay. The diagram shows the percentage of lysed HLA-A2.1+ T2 cells pulsed with either Flu 58–66 peptide or the negative control peptide Melan A/MART 1 27–35.

To further confirm the specificity of the enriched IFN-γ-secreting CD8⁺ T cells from the FLU 58–66 peptide-stimulated PBMC, and to study their cytolytic activity, the cells were expanded for 18 d in tissue culture in the presence of IL-2, and then assayed for CTL activity at an effector: target ratio of 1:1. As shown in FIG. 5, significant killing was observed when target cells were loaded with FLU 58–66 peptide, but not when target cells were loaded with a control peptide (Melan A/MART 1 27–35).

EXAMPLE 7

PBMC from 49 HLA-A2+ individuals were cultured with or without the FLU 58–66 peptide and subjected to the enrichment procedure for IFN-γ-secreting cells as described in Example 3. In 45 cases, on average about 80-fold more IFN-γ-secreting CD8⁺ T cells were isolated from the FLU 58–66 peptide-stimulated sample as compared to the control sample. Only in three cases, no significant difference was detected between both samples. The median frequency of FLU 58–66 peptide-specific CD8⁺ T cells among PBMC, as determined by subtracting the frequencies of the control samples from the frequencies of the FLU 58–66 peptide-stimulated samples, was 1 in 30,000 (range between 1 in 600,000 and 1 in 1000). These results are completely consistent with previous reports in which the frequencies of FLU 58–66 peptide-specific CD8⁺ T cells were determined using enzyme-linked immunospot (ELISPOT) assays for single cell IFN-γ release or tetramers of FLU 58–56 peptide-loaded HLA-A2.1 molecules. Lalvani et al. (1997; and Dunbar et al. (1998).

EXAMPLE 8

To demonstrate that our approach isolates live antigen-specific Th2-type CD4⁺ T cells, PBMC were stimulated with purified TT and IL-4-secreting CD4⁺ T Cells were isolated using an Ab-Ab conjugate directed against CD45 and IL-4. After 10 h of TT stimulation, 150 IL-4-secreting CD4⁺ T cells could be isolated from 2.2×10⁷ PBMC with a purity of 6,89% (FIG. 6). This corresponds to a frequency of TT-specific Th2 cells among total CD4⁺ T cells of 1 in 94,000. The frequency of IL-4-secreting CD4⁺ T Cells in the control culture without TT was about 10 times lower.

All references cited herein, both supra and infra are hereby incorporated herein. Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended claims.

What is claimed is:

1. A method to label antigen-specific T cells with a product secreted and released by the cells, wherein the product is secreted in response to antigen stimulation of said T cells, which method comprises:

a) exposing the antigen-specific T cells to at least one antigen specifically recognized by a T cell receptor under conditions effective to elicit antigen-specific stimulation of at least one antigen-specific T cell;

b) modifying the surface of the antigen-specific T cells to contain a capture moiety specific for the product; and c) culturing the cells, wherein the cells are cultured under conditions wherein the product is secreted, released and specifically bound to the capture moiety, thereby labeling the product-secreting cells, and wherein steps a), b) and c) can be performed in any order or simultaneously.

2. The method according to claim 1 wherein the secreted product specifically bound to the capture moiety. is labeled with a label moiety.

3. The method according to claim 2 wherein the label moiety is an antibody.

4. The method according to claim 1 wherein the capture moiety is an antibody or an antigen-binding fragment thereof.

5. The method according to claim 4 wherein the antibody is bispecific.

6. The method according to claim 1 wherein said capture moiety is coupled to the cell surface of said T-cells through a lipid anchor attached to the capture moiety optionally through a linker moiety.

7. The method according to claim 1 wherein said capture moiety is coupled to the cell surface of said T-cells through an antibody or an antigen-binding fragment thereof attached to the capture moiety optionally through a linker.

8. The method according to claim 5 wherein said bispecific antibody is coupled to the cell surface of said T-cells through specific binding of the antibody to the cell.

9. The method according to claim 1 further comprising the steps of:

determining the amount and type of product label per cell wherein distribution of secreted product type and secretory activity for each secreted product type in a population of cells is determined.

10. A method to label antigen-specific T cells with a product secreted and released by the cells, wherein the product is secreted in response to antigen stimulation of said T cells, which method comprises culturing antigen-specific T cells exposed to at least one antigen; specifically recognized by a T cell receptor under conditions effective to elicit antigen-specific stimulation of at least one antigen-specific T cell and secretion of said product by a stimulated antigen-specific T cell, wherein the surface of the antigen-specific T cell has been modified to contain a capture moiety, wherein said capture moiety is specific for the product and said product specifically binds said capture moiety, thereby labeling the product secreting cells.

11. The method according to claim 10 wherein said antigen-specific T-cells exist within a population of cells.

12. The method according to claim 10 wherein the secreted product is labeled with a label moiety.

13. The method according to claim 12 wherein the label moiety is an antibody.

14. The method according to claim 10 wherein the capture moiety is an antibody or an antigen-binding fragment thereof.

15. The method according to claim 13 wherein the antibody is bispecific.

16. The method according to claim 10 wherein said capture moiety is coupled to the cell surface of said T-cells through a lipid anchor attached to the capture moiety optionally through a linker moiety.

17. The method according to claim 10 wherein said capture moiety is coupled to the cell surface of said T-cells through an antibody or an antigen-binding fragment thereof attached to the capture moiety optionally through a linker.

18. The method according to claim 15 wherein said bispecific antibody is coupled to the cell surface of said T-cells through specific binding of the antibody to the cell.

19. The method according to claim 1, wherein said antigen-specific T-cells exist within a population of cells.

* * * * *